(12) United States Patent
Haeberle et al.

(10) Patent No.: US 8,664,151 B2
(45) Date of Patent: Mar. 4, 2014

(54) ARTICLES COMPRISING REINFORCED POLYURETHANE COATING AGENT

(75) Inventors: Karl Haeberle, Ludwigshafen (DE); Klaus Dieter Hoerner, Ludwigshafen (DE); Jensen Kiziri Buhiru, Mt Healthy, OH (US); Axel Meyer, Schwalbach (DE); Michaela Monika Czupik, Cincinnati, OH (US); Robin Lynn McKiernan, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/461,021

(22) Filed: May 1, 2012

(65) Prior Publication Data

US 2013/0040810 A1      Feb. 14, 2013

Related U.S. Application Data

(60) Provisional application No. 61/491,928, filed on Jun. 1, 2011.

(51) Int. Cl.
*B01J 20/26*      (2006.01)

(52) U.S. Cl.
USPC ........................................... 502/402

(58) Field of Classification Search
USPC ........................................ 502/402; 264/45.1
See application file for complete search history.

(56) References Cited

U.S. PATENT DOCUMENTS

| | | |
|---|---|---|
| 3,479,310 A | 11/1969 | Dieterich et al. |
| 3,905,929 A | 9/1975 | Noll |
| 4,092,286 A | 5/1978 | Noll et al. |
| 4,190,566 A | 2/1980 | Noll et al. |
| 4,541,871 A | 9/1985 | Obayashi et al. |
| 4,666,983 A | 5/1987 | Tsubakimoto et al. |
| 4,959,441 A | 9/1990 | Engelhardt et al. |
| 5,281,683 A | 1/1994 | Yano et al. |
| 5,331,059 A | 7/1994 | Engelhardt et al. |
| 5,409,771 A | 4/1995 | Dahmen et al. |
| 5,532,323 A | 7/1996 | Yano et al. |
| 5,574,121 A | 11/1996 | Irie et al. |
| 5,624,967 A | 4/1997 | Hitomi et al. |
| 5,700,867 A | 12/1997 | Ishiyama et al. |
| 5,837,789 A | 11/1998 | Stockhausen et al. |
| 6,143,821 A | 11/2000 | Houben |
| 6,265,488 B1 | 7/2001 | Fujino et al. |

(Continued)

FOREIGN PATENT DOCUMENTS

| | | |
|---|---|---|
| CA | 2078529 | 3/1993 |
| DE | 2730514 | 1/1979 |

(Continued)

OTHER PUBLICATIONS

International Search Report, PCT/US2012/040062, mailed Sep. 27, 2012, 12 pages.

(Continued)

*Primary Examiner* — Colleen Dunn
*Assistant Examiner* — Haytham Soliman
(74) *Attorney, Agent, or Firm* — Andrew A Paul

(57) ABSTRACT

Articles, such as absorbent articles, are described, comprising a coating or film, for example applied to superabsorbent polymer particles, the coating or film containing a polyurethane polymer material, containing polyurethane polymers with covalently bonded modified silica-containing material.

17 Claims, 3 Drawing Sheets

Fig. 2

(56) References Cited

U.S. PATENT DOCUMENTS

| | | |
|---|---|---|
| 6,472,478 B1 | 10/2002 | Funk et al. |
| 6,503,979 B1 | 1/2003 | Funk et al. |
| 6,559,239 B1 | 5/2003 | Riegel et al. |
| 6,657,015 B1 | 12/2003 | Riegel et al. |
| 6,710,141 B1 | 3/2004 | Heide et al. |
| 6,720,389 B2 | 4/2004 | Hatsuda et al. |
| 6,809,158 B2 | 10/2004 | Ikeuchi et al. |
| 6,911,499 B1 | 6/2005 | Brehm et al. |
| 6,979,564 B2 | 12/2005 | Glucksmann et al. |
| 7,183,360 B2 | 2/2007 | Daniel et al. |
| 7,199,211 B2 | 4/2007 | Popp et al. |
| 7,250,481 B2 | 7/2007 | Jaworek et al. |
| 7,993,829 B2 | 8/2011 | Friedman et al. |
| 8,236,715 B2 | 8/2012 | Schmidt et al. |
| 2003/0195293 A1 | 10/2003 | Lubnin et al. |
| 2004/0177513 A1 | 9/2004 | Vreeland et al. |
| 2004/0214937 A1 | 10/2004 | Lubnin et al. |
| 2005/0033256 A1 | 2/2005 | Schmidt et al. |
| 2005/0043467 A1 | 2/2005 | Bruchmann et al. |
| 2005/0165208 A1 | 7/2005 | Popp et al. |
| 2005/0245684 A1 | 11/2005 | Daniel et al. |
| 2006/0155057 A1 | 7/2006 | Hermeling et al. |
| 2006/0167215 A1 | 7/2006 | Hermeling et al. |
| 2006/0178452 A1 | 8/2006 | Hoefler |
| 2007/0043191 A1 | 2/2007 | Hermeling et al. |
| 2008/0027402 A1 | 1/2008 | Schmidt et al. |
| 2009/0212454 A1 * | 8/2009 | Smith et al. .................. 264/45.1 |

FOREIGN PATENT DOCUMENTS

| | | |
|---|---|---|
| DE | 10204937 | 8/2003 |
| EP | 530438 | 3/1993 |
| EP | 955086 | 9/2003 |
| WO | WO 90/15830 | 12/1990 |
| WO | WO 93/21237 | 10/1993 |
| WO | WO 01/45758 | 6/2001 |
| WO | WO 2005/044900 | 5/2005 |
| WO | WO 2006/042704 | 4/2006 |
| WO | WO 2006/082239 | 8/2006 |
| WO | WO 2007/070776 | 6/2007 |
| WO | WO 2009/016055 | 2/2009 |
| WO | WO 2010/054975 | 5/2010 |
| WO | WO 2012/025445 | 3/2012 |

OTHER PUBLICATIONS

International Search Report, PCT/US2012/039975, mailed Jul. 16, 2012, 12 pages.
U.S. Appl. No. 13/484,705, filed May 31, 2012, Haeberle, et al.
U.S. Appl. No. 13/484,755, filed May 31, 2012, Meyer, et al.
U.S. Appl. No. 13/461,039, filed May 1, 2012, Haeberle, et al.

* cited by examiner

ARTICLES COMPRISING REINFORCED POLYURETHANE COATING AGENT

CROSS REFERENCE TO RELATED APPLICATION

This application claims the benefit of U.S. Provisional Application Ser. No. 61/491,928, filed Jun. 1, 2011, which is herein incorporated by reference in its entirety.

BACKGROUND OF THE INVENTION

Elastomeric polyurethanes are proposed in various product areas, for example as elastomeric films or elastomeric coatings, e.g. elastomeric film coatings. In recent years, superabsorbent polymer particles (SAP, or also referred to as absorbent gelling material, AGM) with elastomeric polyurethane coatings have been proposed. Such coated superabsorbent polymer particles (e.g. when incorporated in an absorbent structure or article) have been found to have a higher gel strength, whilst still having an excellent sorption capacity. (Together with other properties of the swollen polymer particles, gel strength relates to the tendency of the swollen polymer particles to resist deformation under an applied stress. The gel strength needs to be high enough in the absorbent member or article, to reduce deformation and to avoid that the capillary void spaces between the particles are filled to an unacceptable degree, causing so-called gel blocking. This gel blocking inhibits the rate of fluid uptake or the fluid distribution, i.e., once gel blocking occurs, it can substantially impede the distribution of fluids to relatively dry zones or regions in the absorbent article and leakage from the absorbent article can take place well before the water-swellable polymer particles are fully saturated or before the fluid can diffuse or wick past the "blocking" particles into the rest of the absorbent article.)

For example patent applications EP1651283-A and WO2006/083585 describe absorbent articles with superabsorbent polymer particles comprising coatings, e.g. film-coatings, of elastomeric polyurethanes that are extensible even when wet (e.g. when the particles are or have been absorbing fluid), having a high elongation to break, and that are furthermore hydrophilic, to allow sufficient aqueous liquid affinity and that are liquid permeable. Such proposed elastomeric polyurethane coatings can thus effectively extend upon swelling of the particles, and remain substantially complete coatings around the particle, and they can thus effectively reduce deformation of the coated, swollen particle, even when the coating is expanding and wet. Thus, such coatings help to ensure that such particles adopt more spherical shapes upon swelling and allowing more time for the fluid to diffuse through freely through the superabsorbent polymer particles in the absorbent article.

Polyurethane coating and/or films should have good mechanical integrity in terms of durability, in the dry state and preferably in wet state, including when handled in bulk quantities, and they should have a good resistance to tearing, both in dry state and preferably or more importantly in wet state, and they should have good initial elastomeric modulus, along with good propensity to elongate, in the wet state. Furthermore, in some instances, sufficient long term force relaxation may be beneficial, for example for helping to increase the capacity of the coated superabsorbent particles, by lowering the contractive forces on the particles over time.

There is still a need for even higher performance (including for example when wet) elastomeric polyurethane coatings or films in a variety of commercial applications, so that they may be applied in lower amounts and/or so that they may be used as thinner coatings or thinner films.

SUMMARY OF THE INVENTION

The present invention provides articles comprising a film or coating containing a reinforced polyurethane polymer material, said polyurethane polymer material being obtainable by:
  a) obtaining a dispersion or solution of a polyurethane polymer or pre-polymer in a liquid;
  b) I) addition of modified silica-containing material to said dispersion or solution of a), said material being capable of covalently bonding to said polyurethane polymers or pre-polymers; or II) addition of a silica-containing material to said dispersion or solution and addition of a modification material to said dispersion or solution, and thereby obtaining a modified silica-containing material, said material being capable of covalently bonding to said polyurethane polymers or pre-polymers;
  c) optionally addition of a cross-linking agent simultaneous with step a) or b) or subsequent to step b).
  d) optionally addition of a further silica in any of above steps, or subsequent to of said steps.

The polyurethane material and coatings/films are reinforced by the introduction of the modified silica-containing material as described herein. The polyurethane materials herein are found to provide strong coatings (e.g. film coatings) or films of high performance, including when applied onto superabsorbent polymer particles.

In some embodiments, it may be preferred that step b I) above is used.

In some embodiment herein, the polyurethane polymer material herein comprises modified silica, or optionally a combination of further silica (that is not covalently bonded to the polyurethane; herein also referred to as "silica") and modified silica, said modified silica being covalently bonded to the polymeric chains of the polyurethane polymer. It has been found that this may further improve the stress resistance when wet of said films or coatings made of said polyurethane material.

Without being bound by theory, it is believed that the dispersion of the modified-silica in the polyurethane polymer results in a finer morphology of the complex multiphase polyurethanes and can therefore yield a better balance in mechanical properties, especially in the wet state. Furthermore, it has been found that if the modified silica is covalently-bonded to the polyurethane, the tensile stress-strain trade-off, and/or the tear propagation resistance, and/or the long term force relaxation and/or the hydrophilicity (e.g. liquid or liquid vapor permeability) of films or coatings of said polyurethane may be further improved. Thereto, the incorporation of modified silica in the polyurethanes, as described herein, may be very beneficial, optionally combined with the incorporation of silica.

Also the use as film or coating of polyurethane materials comprising mixtures of different polyurethane polymers (e.g. comprising different polyurethane polymers and/or different modified silica-containing material) is envisaged herein.

The polyurethane materials herein can be applied as a coating or as a film, onto a component of the articles, herein, for example applied as a coating onto superabsorbent polymer particles of absorbent articles herein.

DETAILED DESCRIPTION OF THE INVENTION

Modified Silica-Containing Material

Figure 1:
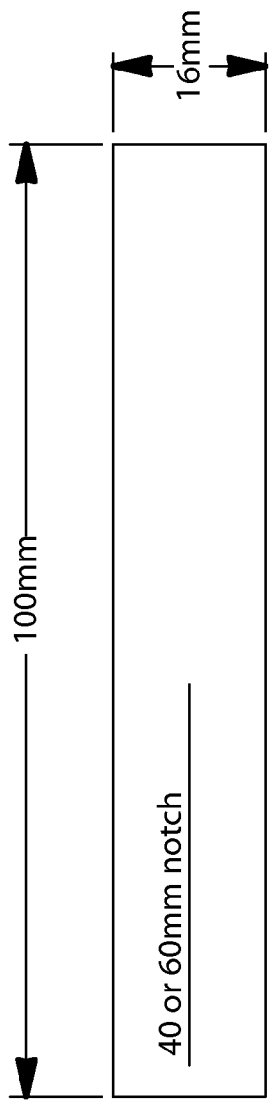
FIG. 1 is a schematic drawing exemplifying how a notched film is made, as described herein.

The modified silica-containing material herein is a silica-containing material that is modified so that it can covalently bond to a polyurethane, as described herein. For example, the polyurethane may comprise polymerized monomers with pending groups that can further bond after polymerization, such as carboxylate or carboxylic acid groups, or the polyurethane may comprise side chains that can further covalently bond to said modified silica-containing material. For example, the modified silica-containing material may comprises a side-chain with a group that can bind to the modified silica-containing material herein, e.g. the side chain having an amine group, or carboxy group, or a carboxylate or carboxylic acid group.

Typically, the modification is an organic group, hence the silica-containing material is for example an organo-modified silica-containing material.

The silica-containing material may be modified to have for example one or more NCO reactive groups, and/or one or more $NR_2$ or $NR_3^+$ groups. R may be any suitable group; in some embodiments each R is independently selected from alkyl, alkenyl, aryl, hydrogen, and one R group may be selected from hydroxy, or aminosubstituted alkylene; in some embodiment, the silica-containing material has one group R that is hydrogen, i.e. NHR or $NHR_2^+$ group, and the other R group or groups are selected from the group as above.

The silica-contain material that is modified herein may be any silica-containing material, such as including clay; preferred may be silica itself. Preferred may be sub-micron silica, e.g. with a weight average particle size of less than 1000 nm, preferably less than 500, preferably up to 200 nm, or preferably up to 100 nm, and typically at least 3 nm, or for example at least 5 nm. Preferred may be so-called fumed silica's, such as AEROSIL® (Degussa).

The silica-containing material may be modified by any method. In some embodiments, to obtain the modified silica-containing material, a modification compound with at least one siloxane group and with at least one NCO reactive group, Compound I, is combined with for example silica. Compound I may be of the general formula I

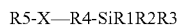   I with
X=O, S, NH
R5=H or alkyl or phenyl or a hydroxy, thio or aminosubstituted alkylene
R4=alkylene having 1 to 12, preferably 1 to three, most preferred 3 C-atoms
R1, R2 and R3 may be identical or different under the proviso that at least one R is an O—R6 with R6 being an alkyl group, preferably methyl or ethyl group. Preferably, all R1, R2 and R3 are O—R6. None, one or two of R1, R2, R3, may be an alkyl group.

Examples for such compounds are 3-aminopropyltrimethoxysilane, 3-aminopropyltriethoxysilane, 2'-aminoethyl-3-aminopropyltrimethoxysilane, 2'-aminoethyl-3-aminopropyltriethoxysilane.

The modification of the silica-containing material can then be done by mixing said material, for example silica, with a modification compound, such as Compound I, for example in a liquid; said liquid typically is inert towards NCO. Preferably, the liquid is propanone, butanone THF, N-methyl pyrrolidone, N-ethyl pyrrolidone, dimethyl formamide or a hydrocarbon.

The weight ratio silica-containing material to the modification compound, e.g. compound I, may, for example be between 100/1 and 1/100.

In some embodiments, the modification is done by adding compound I to a slurry of silica-containing material in a liquid, as those described above.

The weight ratio silica-containing material to liquid in such a slurry may, for example, be in the range from 1:1 to 1/100.

The modified silica-containing material may be added to the polyurethane or pre-polymer thereof, e.g. a dispersion or solution thereto, then covalently bonded to said polyurethane or pre-polymer thereof; or the silica containing material may be added to the polyurethane or prepolymer thereof, e.g. solution or dispersion hereof, and then be modified in said solution or dispersion, and then covalently bonded to said polyurethane or pre-polymer thereof. This may be done at for example room temperature. The reaction may be performed under mechanical stirring. In some embodiments, it may be preferred to use sonication, for example using an Ultrasonic Processor and wand from GE, Model # GE 50 (VDE 0871 Level A), for example up to the maximum amplitude.

In some embodiment, addition of the modified silica-containing material to the dispersion or solution may be preferred.

Any known polyurethane polymer or pre-polymer solution or dispersion can be used herein, such as those described above; in some embodiments it may be preferred to have a dispersion or solution in at least water.

Figure 2:
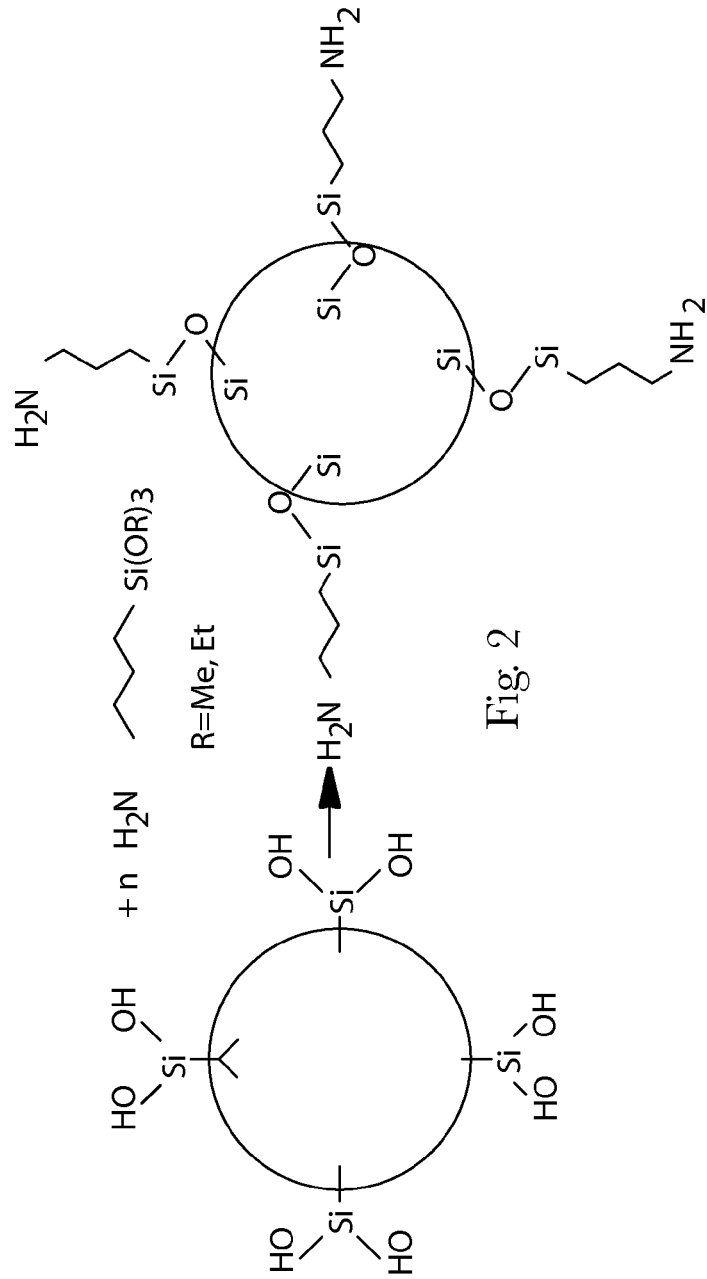
FIG. 2 is a schematic of a silica modification reaction.
Figure 3:
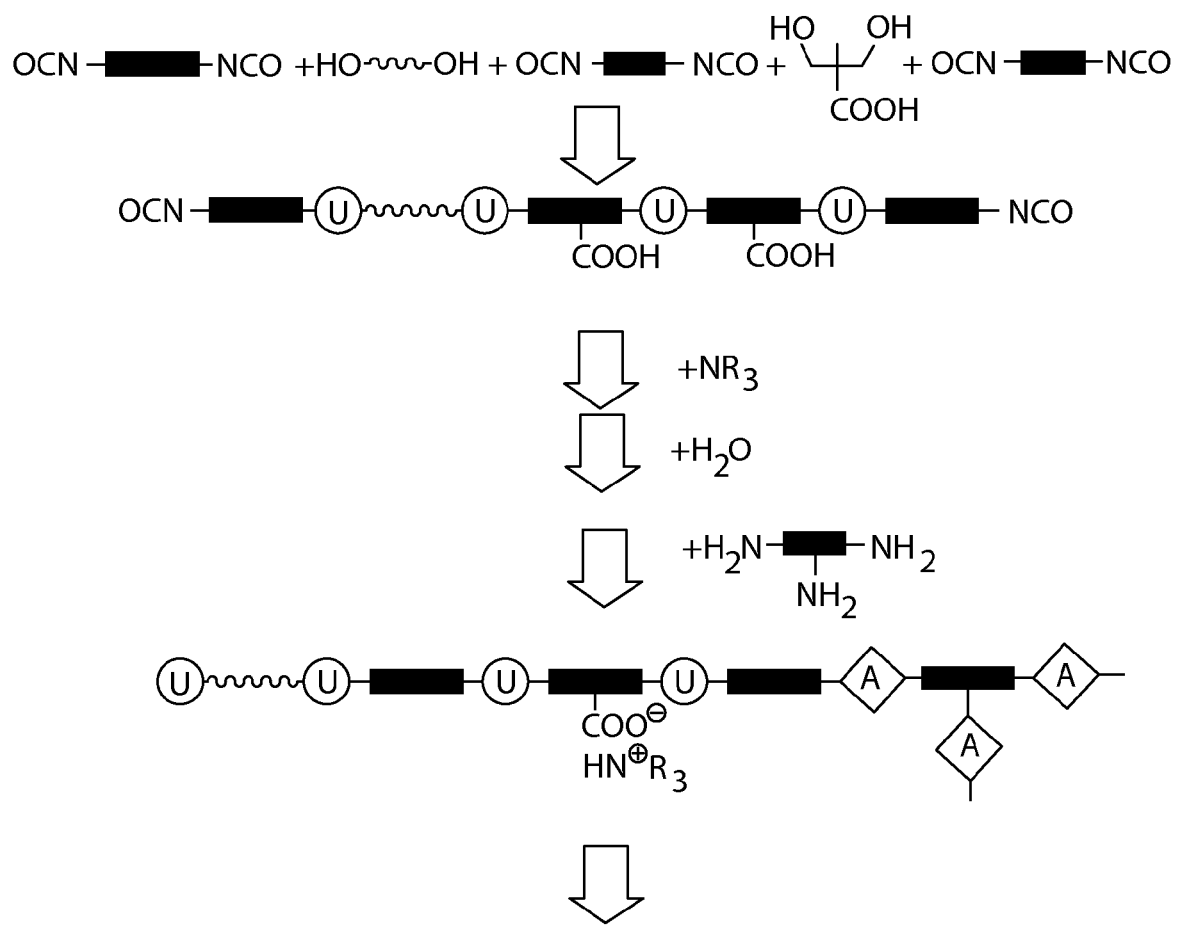
FIG. 3 is a schematic of covalently bonding of modified silica to a polyurethane polymer.
Figure 4:
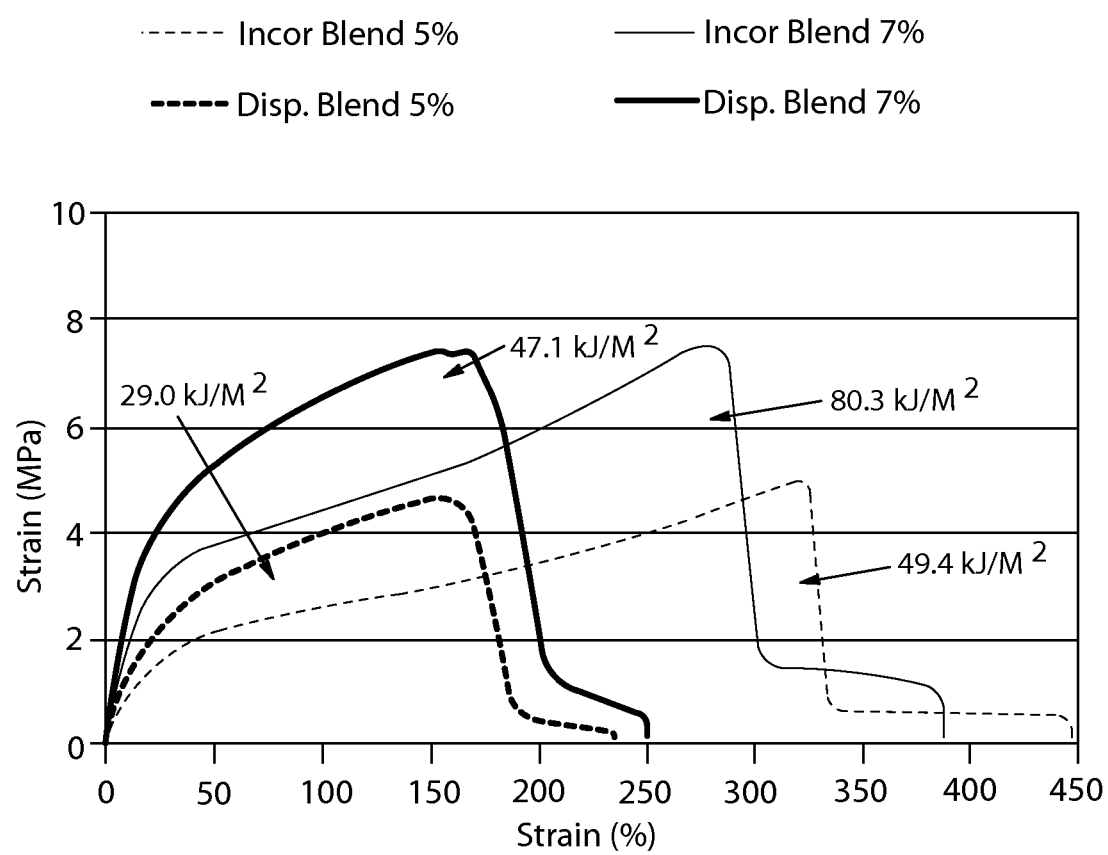
FIG. 4 is a stress-strain curve of materials exemplified in the examples herein.

A schematic overview of the silica modification and covalently bonding thereof to the polyurethane are shown in FIGS. 2 and 3, respectively.

A further silica may be added during any step of the process, including to the polyurethane polymerizations step, or subsequent thereto; said further silica is not modified, and it is hence not covalently bonded to the polyurethane. The further silica may be a hydrophilic silica, i.e. a fumed silica (also referred to as pyrogenic silica), such as an AEROSIL silica. This may further improve the polyurethane film performance, as further described and shown below.

Polyurethane (Pre-) Polymers and Polyurethane Materials

The reinforced polyurethane material comprises polyurethane polymers or pre-polymers, or a polyurethane polymer or pre-polymer mixture, that contains polyurethane polymers or pre-polymers that are covalently bonded to the modified silica-containing material or materials (e.g. mixtures of different modified silica's), obtainable by the process described herein.

The pre-polymers herein are polyurethane oligomers that can be further polymerized to form the desired polyurethane polymers.

The following is described with reference to the polyurethane polymers, but is equally applicable to the pre-polymers, unless stated otherwise.

The polyurethane polymers, and optionally the pre-polymers, and polyurethane material is typically film-forming; this means that the respective polymer or polymeric material can readily be made into a layer or coating upon evaporation of the liquid in which it is dissolved or dispersed, e.g. by a method as for example described below.

The polyurethane polymer, and optionally the pre-polymers, and polyurethane material herein is typically elastomeric; this means that the polymer or polymeric material will exhibit stress-induced deformation that is partially or completely reversed upon removal of the stress. This can be determined by the test method, described below.

The polyurethane polymer and polymeric material is typically such that the resulting coating or film is not water-soluble and, preferably not water-dispersible once a film has been formed. In one embodiment, the polyurethane material herein is preferably such that the resulting coating or film is water-permeable, but not water-soluble and, preferably not water-dispersible.

The synthesis of polyurethanes and the preparation of polyurethane dispersions is well described for example in *Ullmann's Encyclopedia of Industrial Chemistry*, Sixth Edition, 2000 Electronic Release.

It is well understood by those skilled in the art that "polyurethane polymers" is a generic term used to describe polymers that are obtained by reacting di- or polyisocyanates with at least one di- or polyfunctional "active hydrogen-containing" compound. "Active hydrogen containing" means that the di- or polyfunctional compound has at least 2 functional groups which are reactive toward isocyanate groups (also referred to as reactive groups), e.g. hydroxyl groups, primary and secondary amino groups and mercapto (SH) groups, but preferably hydroxyl groups or amino groups, or in some embodiments, preferably hydroxyl groups. It also is well understood by those skilled in the art that polyurethanes also include allophanate, biuret, carbodiimide, oxazolidinyl, isocyanurate, uretdione, and other linkages in addition to urethane and urea linkages.

The polyurethane material and films or coatings thereof may be hydrophilic and in particular surface hydrophilic. They may be characterized by a contact angle that is less than 90 degrees. Contact angles can for example be measured with the Video-based contact angle measurement device, Krüss G10-G1041, available from Kruess, Germany or by other methods known in the art.

In one preferred embodiment, the hydrophilic properties are achieved as a result of the polyurethane comprising hydrophilic polymer blocks, for example polyether groups having a fraction of groups derived from ethylene glycole ($CH_2CH_2O$) or from 1,2-propanediole ($—CH(CH_3)—CH_2O—$), or mixtures thereof. Polyether polyurethanes are therefore preferred film-forming polymers. The hydrophilic blocks can be constructed in the manner of comb polymers where parts of the side chains or all side chains are hydrophilic polymeric blocks. But the hydrophilic blocks can also be constituents of the main chain (i.e., of the polymer's backbone). A preferred embodiment utilizes polyurethanes where at least the predominant fraction of the hydrophilic polymeric blocks is present in the form of side chains. The side chains can in turn be polyethylene glycol or block copolymers such as poly(ethylene glycol)-co-polypropylene glycol). If poly(ethylene glycol)-co-polypropylene glycol) copolymers are used, then the content of ethylene oxide units should be at least 50 mole %, preferably at least 65 mole %.

It is further possible to obtain hydrophilic properties for the polyurethanes through an elevated fraction of ionic groups, preferably carboxylate, sulfonate, phosphonate or ammonium groups. The ammonium groups may be protonated or alkylated tertiary or quarternary groups. Carboxylates, sulfonates, and phosphates may be present as alkali-metal or ammonium salts. Suitable ionic groups and their respective precursors are for example described in *Ullmanns Encyclopädie der technischen Chemie*, 4$^{th}$ Edition, Volume 19, p. 311-313 and are furthermore described in DE-A 1 495 745 and WO 03/050156.

The hydrophilicity of the preferred polyurethanes facilitates the penetration and dissolution of water into the superabsorbent polymeric particles, which are enveloped by the film-forming polymer. The present invention's coatings with these preferred polyurethanes are notable for the fact that the mechanical properties are not excessively impaired even in the moist state, despite the hydrophilicity.

Preferred film forming polymers have two or more glass transition temperatures (Tg) (determined by DSC). Ideally, the polymers used exhibit the phenomenon of phase separation, i.e., they contain two or more different blocks of low and high Tg side by side in the polymer (*Thermoplastic Elastomers: A Comprehensive Review*, eds. Legge, N. R., Holden, G., Schroeder, H. E., 1987, chapter 2). However, the measurement of Tg may in practice be very difficult in cases when several Tg's are close together or for other experimental reasons. Even in cases when the Tg's cannot be determined clearly by experiment the polymer may still be suitable in the scope of the present invention.

Especially preferred phase-separating polymers herein comprise one or more phase-separating block copolymers, having a weight average molecular weight Mw of at least 5 kg/mol, preferably at least 10 kg/mol and higher.

In another embodiment, especially with polyurethanes, such a block copolymer has at least a first polymerized polymer segment (block) and a second polymerized polymer segment (block), polymerized with one another, whereby preferably the first (soft) segment has a $Tg_1$ of less than 25° C. or even less than 20° C., or even less than 0° C., and the second (hard) segment has a $Tg_2$ of at least 50° C., or of 55° C. or more, preferably 60° C. or more or even 70° C. or more.

The preferred weight average molecular weight of a first (soft) segment (with a Tg of less than 25° C.) is at least 500 g/mol, preferably at least 1000 g/mol or even at least 2000 g/mol, but preferably less than 8000 g/mol, preferably less than 5000 g/mol.

However, the total of the first (soft) segments is typically 20% to 95% by weight of the total block copolymer, or even from 20% to 85% or more preferably from 30% to 75% or even from 40% to 70% by weight. Furthermore, when the total weight level of soft segments is more than 70%, it is even more preferred that an individual soft segment has a weight average molecular weight of less than 5000 g/mol.

In one embodiment the block copolymers useful herein are preferably polyether urethanes and polyester urethanes. Especially preferred are polyether urethanes comprising polyalkylene glycol units, especially polyethylene glycol units or poly(tetramethylene glycol) units.

In one preferred embodiment polyester urethanes are used as they often exhibit better mechanical properties in the wet state when compared to polyether urethanes.

As used herein, the term "alkylene glycol" includes both alkylene glycols and substituted alkylene glycols having 2 to 10 carbon atoms, such as ethylene glycol, 1,3-propylene glycol, 1,2-propylene glycol, 1,2-butylene glycol, 1,3-butylene glycol, 1,4-butylene glycol, styrene glycol and the like.

The polyurethanes used according to the present invention are generally obtained by reaction of polyisocyanates with active hydrogen-containing compounds having two or more reactive groups. These include
  a) high molecular weight compounds having a molecular weight in the range of preferably 300 to 100 000 g/mol especially from 500 to 30 000 g/mol
  b) low molecular weight compounds and
  c) compounds having polyether groups, especially polyethylene oxide groups or polytetrahydrofuran groups and a molecular weight in the range from 200 to 20 000 g/mol, the polyether groups in turn having no reactive groups.

These compounds can also be used as mixtures.

Suitable polyisocyanates have an average of about two or more isocyanate groups, preferably an average of about two to about four isocyanate groups and include aliphatic, cycloaliphatic, araliphatic, and aromatic polyisocyanates, used alone or in mixtures of two or more. Diisocyanates are more preferred. Especially preferred are aliphatic and cycloaliphatic polyisocyanates, especially diisocyanates.

Specific examples of suitable aliphatic diisocyanates include alpha, omega-alkylene diisocyanates having from 5 to 20 carbon atoms, such as 1,6-hexamethylene diisocyanate, 1,12-dodecane diisocyanate, 2,2,4-trimethylhexamethylene diisocyanate, 2,4,4-trimethyl-hexamethylene diisocyanate, 2-methyl-1,5-pentamethylene diisocyanate, and the like. Polyisocyanates having fewer than 5 carbon atoms can be used but are less preferred because of their high volatility and toxicity. Preferred ali-phatic polyisocyanates include 1,6-hexamethylene diisocyanate, 2,2,4-trimethyl-hexamethylene diisocyanate, and 2,4,4-trimethyl-hexamethylene diisocyanate.

Specific examples of suitable cycloaliphatic diisocyanates include dicyclohexylmethane diisocyanate, (commercially available as Desmodur® W from Bayer Corporation), isophorone diisocyanate, 1,4-cyclohexane diisocyanate, 1,3-bis(isocyanatomethyl)cyclohexane, and the like. Preferred cycloaliphatic diisocyanates include dicyclohexylmethane diisocyanate and isophorone diisocyanate.

Specific examples of suitable araliphatic diisocyanates include m-tetramethyl xylylene diisocyanate, p-tetramethyl xylylene diisocyanate, 1,4-xylylene diisocyanate, 1,3-xylylene diisocyanate, and the like. A preferred araliphatic diisocyanate is tetramethyl xylylene diisocyanate.

Examples of suitable aromatic diisocyanates include 4,4'-diphenylmethane diisocyanate, toluene diisocyanate, their isomers, naphthalene diisocyanate, and the like. A preferred aromatic diisocyanate is toluene diisocyanate and 4,4'-diphenylmethane diisocyanate.

Examples of high molecular weight compounds a) having 2 or more reactive groups are such as polyester polyols and polyether polyols, as well as polyhydroxy polyester amides, hydroxyl-containing polycaprolactones, hydroxyl-containing acrylic copolymers, hydroxyl-containing epoxides, polyhydroxy polycarbonates, polyhydroxy polyacetals, polyhydroxy polythioethers, polysiloxane polyols, ethoxylated polysiloxane polyols, polybutadiene polyols and hydrogenated polybutadiene polyols, polyacrylate polyols, halogenated polyesters and polyethers, and the like, and mixtures thereof. The polyester polyols, polyether polyols, polycarbonate polyols, polysiloxane polyols, and ethoxylated polysiloxane polyols are preferred. Particular preference is given to polyesterpolyols, polycarbonate polyols, polyalkylene ether polyols, and polytetrahydrofurane. The number of functional groups in the aforementioned high molecular weight compounds is preferably on average in the range from 1.8 to 3 and especially in the range from 2 to 2.2 functional groups per molecule.

The polyester polyols typically are esterification products prepared by the reaction of organic polycarboxylic acids or their anhydrides with a stoichiometric excess of a diol.

The diols used in making the polyester polyols include alkylene glycols, e.g., ethylene glycol, 1,2- and 1,3-propylene glycols, 1,2-, 1,3-, 1,4-, and 2,3-butane diols, hexane diols, neopentyl glycol, 1,6-hexanediol, 1,8-octanediol, and other diols such as bisphenol-A, cyclohexanediol, cyclohexane dimethanol (1,4-bis-hydroxymethylcycohexane), 2-methyl-1,3-propanediol, 2,2,4-trimethyl-1,3-pentanediol, diethylene glycol, triethylene glycol, tetraethylene glycol, polyethylene glycol, dipropylene glycol, polypropylene glycol, dibutylene glycol, polybutylene glycol, dimerate diol, hydroxylated bisphenols, polyether glycols, halogenated diols, and the like, and mixtures thereof. Preferred diols include ethylene glycol, diethylene glycol, butane diol, hexane diol, and neopentylglycol. Alternatively or in addition, the equivalent mercapto compounds may also be used.

Suitable carboxylic acids used in making the polyester polyols include dicarboxylic acids and tricarboxylic acids and anhydrides, e.g., maleic acid, maleic anhydride, succinic acid, glutaric acid, glutaric anhydride, adipic acid, suberic acid, pimelic acid, azelaic acid, sebacic acid, chlorendic acid, 1,2,4-butane-tricarboxylic acid, phthalic acid, the isomers of phthalic acid, phthalic anhydride, fumaric acid, dimeric fatty acids such as oleic acid, and the like, and mixtures thereof. Preferred polycarboxylic acids used in making the polyester polyols include aliphatic or aromatic dibasic acids.

Examples of suitable polyester polyols include poly(glycol adipate)s, poly(ethylene terephthalate) polyols, polycaprolactone polyols, orthophthalic polyols, sulfonated and phosphonated polyols, and the like, and mixtures thereof.

The preferred polyester polyol is a diol. Preferred polyester diols include poly(butanediol adipate); hexanediol adipic acid and isophthalic acid polyesters such as hexaneadipate isophthalate polyester; hexanediol neopentyl glycol adipic acid polyester diols, e.g., Piothane 67-3000 HNA (Panolam Industries) and Piothane 67-1000 HNA, as well as propylene glycol maleic anhydride adipic acid polyester diols, e.g., Piothane SO-1000 PMA, and hexane diol neopentyl glycol fumaric acid polyester diols, e.g., Piothane 67-SO0 HNF. Other preferred Polyester diols include Rucoflex® S101.5-3.5, S1040-3.5, and S-1040-110 (Bayer Corporation).

Polyether polyols are obtained in known manner by the reaction of a starting compound that contain reactive hydrogen atoms, such as water or the diols set forth for preparing the polyester polyols, and alkylene glycols or cyclic ethers, such as ethylene glycol, propylene glycol, butylene glycol, styrene glycol, ethylene oxide, propylene oxide, 1,2-butylene oxide, 2,3-butylene oxide, oxetane, tetrahydrofuran, epichlorohydrin, and the like, and mixtures thereof. Preferred polyethers include poly(ethylene glycol), polypropylene glycol), polytetrahydrofuran, and co [poly(ethylene glycol)-polypropylene glycol)]. Polyethylenglycol and Polypropyleneglycol can be used as such or as physical blends. In case that propyleneoxide and ethylenoxide are copolymerized, these polypropylene-co-polyethylene polymers can be used as random polymers or block-copolymers.

In one embodiment the polyetherpolyol is a constituent of the main polymer chain. In another embodiment the polyesterpolyole is a constituent of the main polymer chain. In a preferred embodiment the polyetherpolyol and the polyesterpolyol are both constituents of the main polymer chain.

In another embodiment the polyetherol is a terminal group of the main polymer chain.

In yet another embodiment the polyetherpolyol is a constituent of a side chain which is comb-like attached to the main chain. An example of such a monomer is Tegomer D-3403 (Degussa).

Polycarbonates include those obtained from the reaction of diols such 1,3-propanediol, 1,4-butanediol, 1,6-hexanediol, diethylene glycol, triethylene glycol, tetraethylene glycol, and the like, and mixtures thereof with dialkyl carbonates such as diethyl carbonate, diaryl carbonates such as diphenyl carbonate or phosgene.

Examples of low molecular weight compounds b) having two reactive functional groups are the diols such as alkylene glycols and other diols mentioned above in connection with the preparation of polyesterpolyols. They also include diamines such as diamines and polyamines, which are among the preferred compounds useful in preparing the polyesteramides and polyamides. Suitable diamines and polyamines include 1,2-diaminoethane, 1,6-diaminohexane, 2-methyl-L5-pentanediamine, 2,2,4-trimethyl-1,6-hexanediamine, 1,12-diaminododecane, 2-aminoethanol, 2-[(2-aminoethyl) amino]-ethanol, piperazine, 2,5-dimethylpiperazine, 1-amino-3-aminomethyl-3,5,5-trimethylcyclohexane (isophorone diamine or IPDA), bis-(4-aminocyclohexyl)-methane, bis-(4-amino-3-methyl-cyclohexyl)-methane, 1,4-diaminocyclohexane, 1,2-propylenediamine, hydrazine, urea, amino acid hydrazides, hydrazides of semicarbazidocarboxylic acids, bis-hydrazides and bis-semicarbazides, diethylene triamine, triethylene tetramine, tetraethylene pentamine, pentaethylene hexamine, N,N,N-tris-(2-aminoethyl)amine, N-(2-piperazinoethyl)-ethylene diamine, N,N'-bis-(2-aminoethyl)-piperazine, N,N,N'-tris-(2-aminoethyl)ethylene diamine, N—[N-(2-aminoethyl)-2-aminoethyl]-N'-(2-aminoethyl)-piperazine, N-(2-aminoethyl)-N'-(2-piperazinoethyl)-ethylene diamine, N,N-bis-(2-aminoethyl)-N-(2-piperazinoethyl)amine, N,N-bis-(2-piperazinoethyl)amine, polyethylene imines, iminobispropylamine, guanidine, melamine, N-(2-aminoethyl)-1,3-propane diamine, 3,3'-diaminobenzidine, 2,4,6-triaminopyrimidine, polyoxypropylene amines, tetrapropylenepentamine, tripropylenetetramine, N,N-bis-(6-aminohexyl)amine, N,N'-bis-(3-aminopropyl)ethylene diamine, and 2,4-bis-(4'-aminobenzyl)-aniline, and the like, and mixtures thereof. Preferred diamines and polyamines include 1-amino-3-aminomethyl-3,5,5-trimethyl-cyclohexane (isophorone diamine or IPDA), bis-(4-aminocyclohexyl)-methane, bis-(4-amino-3-methylcyclohexyl)-methane, ethylene diamine, diethylene triamine, triethylene tetramine, tetraethylene pentamine, and pentaethylene hexamine, and the like, and mixtures thereof. Other suitable diamines and polyamines for example include JEFFAMINE® D-2000 and D-4000, which are amine-terminated polypropylene glycols differing only by molecular weight, and JEFFAMINE® XTJ-502, T 403, T 5000, and T 3000 which are amine terminated polyethyleneglycols, amine terminated co-polypropylene-polyethylene glycols, and triamines based on propoxylated glycerol or trimethylol-propane and which are available from Huntsman Chemical Company.

The poly(alkylene glycol) may be part of the polymer main chain or be attached to the main chain in comb-like shape as a side chain.

In a preferred embodiment, the polyurethane comprises poly(alkylene glycol) side chains sufficient in amount to comprise about 10 wt. % to 90 wt. %, preferably about 12 wt. % to about 80 wt. %, preferably about 15 wt. % to about 60 wt. %, and more preferably about 20 wt. % to about 50 wt. %, of poly(alkylene glycol) units in the final polyurethane on a dry weight basis. At least about 50 wt. %, preferably at least about 70 wt. %, and more preferably at least about 90 wt. % of the poly(alkylene glycol) side-chain units comprise poly(ethylene glycol), and the remainder of the side-chain poly-(alkylene glycol) units can comprise alkylene glycol and substituted alkylene glycol units having from 3 to about 10 carbon atoms. The term "final polyurethane" means the polyurethane used for coating the superabsorbent polymeric particles.

Preferably the amount of the side-chain units is (i) at least about 30 wt. % when the molecular weight of the side-chain units is less than about 600 g/mol, (ii) at least about 15 wt. % when the molecular weight of the side-chain units is from about 600 to about 1000 g/mol, and (iii) at least about 12 wt. % when the molecular weight of said side-chain units is more than about 1000 g/mol. Mixtures of active hydrogen-containing compounds having such poly(alkylene glycol) side chains can be used with active hydrogen-containing compounds not having such side chains.

These side chains can be incorporated in the polyurethane by replacing a part or all of the aforementioned high molecular diols a) or low molecular compounds b) by compounds c) having at least two reactive functional groups and a polyether group, preferably a polyalkylene ether group, more preferably a polyethylene glycol group that has no reactive group.

For example, active hydrogen-containing compounds having a polyether group, in particular a poly(alkylene glycol) group, include diols having poly(ethylene glycol) groups such as those described in U.S. Pat. No. 3,905,929 (incorporated herein by reference in its entirety). Further, U.S. Pat. No. 5,700,867 (incorporated herein by reference in its entirety) teaches methods for incorporation of poly(ethylene glycol) side chains at col. 4, line 3.5 to col. 5, line 4.5. A preferred active hydrogen-containing compound having poly(ethylene glycol) side chains is trimethylol propane mono (polyethylene oxide methyl ether), available as TEGOMER D-3403 from Degussa-Goldschmidt. Another method to incorporate poly(ethylene glycol) as a side chain into the main polymer chain is described in DE 2 730 514 (incorporated herein by reference in its entirety). According to this method a diisocyanate having two isocyanate groups of different reactivity is reacted with a HO-monofunctional poly(ethyleneoxide) in stoichiometric ratio (1 mole:1 mole), and subsequently the second isocyanate group is reacted in stoichiometric ratio (1 mole:1 mole) with a dialkanoleamine to form a diole. Such diole can be then incorporated by the conventional techniques. Suitable isocyanates are for example isophoronediisocyanate, a suitable dialkanoleamine is diethanolamine.

Preferably, the polyurethanes to be used in the present invention also have reacted therein at least one active hydrogen-containing compound not having said side chains and typically ranging widely in molecular weight from about 50 to about 10000 g/mol, preferably about 200 to about 6000 g/mol, and more preferably about 300 to about 3000 g/mol. Suitable active hydrogen-containing compounds not having said side chains include any of the amines and polyols described herein as compounds a) and b).

According to one preferred embodiment of the invention, the active hydrogen compounds are chosen to provide less than about 25 wt. %, more preferably less than about 15 wt. % and most preferably less than about 5 wt. % poly(ethylene glycol) units in the backbone (main chain) based upon the dry weight of final polyurethane, since such main-chain poly(ethylene glycol) units tend to cause swelling of polyurethane particles in the waterborne polyurethane dispersion and also contribute to lower in use tensile strength of articles made from the polyurethane dispersion.

The preparation of polyurethanes having polyether side chains is known to one skilled in the art and is extensively described for example in US 2003/0195293, which is hereby expressly incorporated herein by reference.

Advantageous polyurethanepolymers herein are obtained by first preparing prepolymers having isocyanate end groups, which are subsequently linked together in a chain-extending step. The linking together can be through water or through reaction with a compound having at least one crosslinkable functional group. The modified silica-containing material may then be added to the pre-polymers prior to forming the final polymers.

The pre-polymer is obtained by reacting one of the above-described isocyanate compounds with an active hydrogen compound. Preferably the pre-polymer is prepared from the abovementioned polyisocyanates, at least one compound c) and optionally at least one further active hydrogen compound selected from the compounds a) and b).

In one embodiment the ratio of isocyanate to active hydrogen in the compounds forming the prepolymer typically ranges from about 1.3/1 to about 2.5/1, preferably from about 1.5/1 to about 2.1/1, and more preferably from about 1.7/1 to about 2/1.

The polyurethane may additionally contain functional groups which can undergo further crosslinking reactions and which can optionally render them self-crosslinkable.

Compounds having at least one additional crosslinkable functional group include those having carboxylic, carbonyl, amine, hydroxyl, and hydrazide groups, and the like, and mixtures of such groups. The typical amount of such optional compound is up to about 1 milliequivalent, preferably from about 0.05 to about 0.5 milliequivalents, and more preferably from about 0.1 to about 0.3 milliequivalent per gram of final polyurethane on a dry weight basis.

The preferred monomers for incorporation into the isocyanate-terminated prepolymer are hydroxy-carboxylic acids having the general formula $(HO)_x Q(COOH)_y$ wherein Q is a straight or branched hydrocarbon radical having 1 to 12 carbon atoms, and x and y are 1 to 3. Examples of such hydroxycarboxylic acids include citric acid, dimethylolpro-panoic acid (DMPA), dimethylol butanoic acid (DMBA), glycolic acid, lactic acid, malic acid, dihydroxymalic acid, tartaric acid, hydroxypivalic acid, and the like, and mixtures thereof. Dihydroxy-carboxylic acids are more preferred with dimethylolpropanoic acid (DMPA) being most preferred.

Other suitable compounds providing crosslinkability include thioglycolic acid, 2,6-dihydroxybenzoic acid, and the like, and mixtures thereof.

Optional neutralization of the pre-polymer having pendant carboxyl groups converts the carboxyl groups to carboxylate anions, thus having a water-dispersibility enhancing effect. Suitable neutralizing agents include tertiary amines, metal hydroxides, ammonia, and other agents well known to those skilled in the art.

As a chain extender, at least one of water, an inorganic or organic polyamine having an average of about 2 or more primary and/or secondary amine groups, polyalcohols, ureas, or combinations thereof is suitable for use in the present invention. Suitable organic amines for use as a chain extender include diethylene triamine (DETA), ethylene diamine (EDA), meta-xylylenediamine (MXDA), aminoethyl ethanolamine (AEEA), 2-methyl pentane diamine, isophorondiamine (IPDA), and the like, and mixtures thereof. Also suitable for practice in the present invention are propylene diamine, butylene diamine, hexamethylene diamine, cyclohexylene diamine, phenylene diamine, tolylene diamine, 3,3-dichlorobenzidene, 4,4'-methylene-bis-(2-chloroaniline), 3,3-dichloro-4,4-diamino diphenylmethane, sulfonated primary and/or secondary amines, and the like, and mixtures thereof. Suitable inorganic and organic amines include hydrazine, substituted hydrazines, and hydrazine reaction products, and the like, and mixtures thereof. Suitable polyalcohols include those having from 2 to 12 carbon atoms, preferably from 2 to 8 carbon atoms, such as ethylene glycol, diethylene glycol, neopentyl glycol, butanediols, hexanediol, and the like, and mixtures thereof. Suitable ureas include urea and its derivatives, and the like, and mixtures thereof. Hydrazine is preferred and is most preferably used as a solution in water.

The amount of chain extender typically ranges from about 0.5 to about 0.95 equivalents based on available isocyanate.

A degree of branching of the polyurethane may be beneficial, but is not required to maintain a high tensile strength and improve resistance to creep (cf. strain relaxation). This degree of branching may be accomplished during the prepolymer step or the extension step. For branching during the extension step, the chain extender DETA is preferred, but other amines having an average of about two or more primary and/or secondary amine groups may also be used. For branching during the prepolymer step, it is preferred that trimethylol propane (TMP) and other polyols having an average of more than two hydroxyl groups be used. The branching monomers can be present in amounts up to about 4 wt. % of the polymer backbone.

Preferred aqueous polyurethane dispersions useful herein are Hauthane HD-4638 (ex Hauthaway), HYDROLAR® HC 269 (ex COIMolm, Italy), IMPRAPERM® 48180 (ex Bayer Material Science AG, Germany), LURAPRET® DPS (ex BASF Aktiengesellschaft, Germany), ASTACIN® Finish LD 1603 (ex BASF Aktiengesellschaft, Germany), PERMAX® 120, PERMAX 200, and PERMAX 220 (ex Noveon, Brecksville, Ohio), Syntegra YM2000 and Syntegra YM2100 (ex Dow, Midland, Mich.), WITCOBOND® G-213, WITCOBOND G-506, WITCOBOND G-507, WITCOBOND 736 (ex Uniroyal Chemical, Middlebury, Conn.), ASTACIN Finish PUMN TF, ASTACIN TOP 140, ASTACIN Finish SUSI (all ex BASF) and IMPRANIL® DLF (anionic aliphatic polyester-polyurethan dispersion from Bayer Material Science)

Particularly hydrophilic thermoplastic polyurethanes are sold by Noveon, Brecksville, Ohio, under the tradenames of PERMAX 120, PERMAX 200 and PERMAX 220 and are described in detail in *Proceedings International Waterborne High Solids Coatings,* 32, 299, 2004 and were presented to the public in February 2004 at the "International Waterborne, High-Solids, and Powder Coatings Symposium" in New Orleans, USA. The preparation is described in detail in US 2003/0195293.

More particularly, the polyurethanes described can be used in mixtures with each other or with other film-forming polymers, fillers, oils, blowing aids, water-soluble polymers or plasticizing agents in order that particularly advantageous properties may be achieved with regard to hydrophilicity, water perviousness and mechanical properties. Polymers that are suitable for blending with polyurethane dispersions are in many cases also suitable to accomplish a sufficiently good coating when used alone.

In a particularly preferred embodiment the film forming polymer dispersion, most preferably a polyurethane dispersion, is blended with at least one other polymer dispersion selected for example from poly-co(ethylene-vinylacetate), polyacetale and homo- and copolymers comprising acrylonitrile, butadiene, styrene, (meth-)acrylate, isoprene or vinylpyrrolidone. (Meth-)acrylate shall mean methacrylic acid and acrylic acid and all their respective derivatives, especially their esters. Blending can be done in any ratio, however particularly preferred are blending ratios that will lead to films on the water absorbing polymeric particles which yield comparable performance properties of the coated superabsorbent polymeric particles as would have otherwise been obtained by a coating with the unblended film forming polymers. Examples of such suitable dispersion for blending are LEPTON® TOP LB (aqueous polyacrylate and wax dispersion, BASF Aktiengesellschaft), Airflex EP 17V (aqueous Vinylacetate-Ethylene-Copolymer dispersion, Air Products B.V.), EPOTAL® 480 (aqueous styrene-acrylonitrile-acrylate dispersion, BASF Aktiengesellschaft), POLIGEN® MA (hard film forming aqueous polyacrylate dispersion, BASF Aktiengesellschaft), CORIAL® Binder OK (medium hard film forming aqueous polyacrylate dispersion, BASF Aktiengesellschaft), CORIAL Binder IF (soft film forming aqueous polyacrylate dispersion, BASF Aktiengesellschaft), CORIAL ULTRASOFT NT (very soft film forming aqueous polyacrylate dispersion, BASF Aktiengesellschaft) and MOWILITH® DM 799 from Celanese Emulsion GmbH (hard film forming anionic stabilized Acryl-/Methacrylate Polymer dispersion, OH-number ~18 [b.o. polymer], MFT ~90° C., Tg ~110° C.)

Articles Including Absorbent Articles

The articles of the invention comprise a coating or film containing the specific polyurethane polymer material as described herein. Such an article may for example be a hygiene article comprising a component that is coated with such a coating agent. The article may for example be a razor with a razor head comprising the coating or film herein.

The article may also for example be an absorbent article comprising a article component containing the coating or film herein, for example such a component may be a nonwoven sheet or web material, or preferably said component may be superabsorbent polymeric particles. Such sheet, webs or particles may then comprise a coating or film of the polyurethane material herein.

The polyurethane material can be made into a film and then applied to the component of the article herein; alternatively the polyurethane material can be directly applied and (hence coated) onto the component of the article herein. Typically, this is done by applying a solution or dispersion of the polyurethane material herein.

The coating, as used herein, may be a partial coating a complete coating, and/or it may include network coatings.

"Absorbent article" refers to devices that absorb and retain liquids (such as blood and urine), and more specifically, refers to devices that are placed against or in proximity to the body of the wearer to absorb and contain the various exudates discharged from the body. Absorbent articles include but are not limited to adult and infant diapers, including training pants, adult incontinence pads, diaper holders and liners, sanitary napkins and the like. "Diaper" refers to an absorbent article generally worn by infants and adult incontinent persons about the lower torso. "Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

The absorbent article comprises typically an absorbent structure to absorb and retain liquids, such as urine or blood. The absorbent structure typically comprises the coated superabsorbent polymeric particles described herein and a structuring material, and a support layer(s). The absorbent structure may be the storage layer of an absorbent article, or the acquisition layer, or both, either as two or more layers or as unitary structure.

The support layer (s) may be foam, film, woven web and/or nonwoven web, as known in the art, including spunbond, meltblown and/or carded nonwovens and laminates thereof. One preferred material is a so-called nonwoven laminates material, one or more melt-blown between two or more spunbonded layer. Preferred non-woven materials are provided from synthetic fibers, such as PE, PET and most preferably PP.

The absorbent structure may also comprise a structuring agent, such as absorbent fibrous material, such as absorbent cellulose fibers, and/or an adhesive, for example a fibrous adhesive, and/or thermoplastic fibrous material, which each may serve to immobilize the superabsorbent material. It may be preferred that said absorbent structure herein comprises large amounts of the superabsorbent material herein and only very little or no absorbent cellulose fibers, preferably less than 10% by weight of the superabsorbent material herein, or preferably even less than 5% by weight.

Preferred absorbent structures herein comprise a layer of a support material, and thereon a superabsorbent polymeric particulate material (as described herein) layer, optionally as a discontinuous layer, and thereon a layer of an adhesive or thermoplastic material or preferably a thermoplastic adhesive material, e.g. in the form of fibers, which is applied onto the layer of said superabsorbent polymeric particulate material The thermoplastic adhesive may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants. The thermoplastic polymer has typically a molecular weight (Mw) of more than 10,000 and a glass transition temperature (Tg) usually below room temperature. A wide variety of thermoplastic polymers are suitable for use in the present invention. Such thermoplastic polymers are preferably water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

The additional resin has typically a Mw below 5,000 and a Tg usually above room temperature, typical concentrations of the resin in a hot melt are in the range of 30-60%. The plasticizer has a low Mw of typically less than 1,000 and a Tg below room temperature, a typical concentration is 0-15%.

Preferably, the adhesive is present in the forms of fibres throughout the absorbent structure, i.e. the adhesive is fiberized. Preferably, the fibres will preferably have an average thickness of 1-50 micrometer and an average length of 5 mm to 50 cm.

Preferably, the absorbent structure, in particular when no or little absorbent fibres are present, as described above, has a density greater than about $0.4 \text{ g/cm}^3$. Preferably, the density is greater than about $0.5 \text{ g/cm}^3$, more preferably greater than about $0.6 \text{ g/cm}^3$.

Preferred absorbent structures can for example be made as follows:
  a) providing a substrate material, e.g. that can serve as a wrapping material;

b) depositing the superabsorbent polymeric particulate material as described herein, comprising a coating of said polyurethane material herein, onto a first surface of the substrate material, c) depositing a thermoplastic and/or adhesive material onto the superabsorbent polymeric particulate material, d) and then typically closing the above structure by folding the substrate material over, or by placing another substrate matter over the above, or by repeating step a) and b) and c) to form a second structure, that is placed onto the first structure, so that the coated particles and adhesive are sandwiched between the two substrate materials.

The absorbent structure of the invention may be, or may be part of an absorbent article, typically it may be the absorbent core of an absorbent article, or the storage layer and/or acquisition layer of such an article.

Preferred (disposable) absorbent article comprising the absorbent structure of the invention are sanitary napkins, panty liners, adult incontinence products and infant diapers or training or pull-on pants, whereby articles which serve to absorb urine, e.g. adult incontinence products, diapers and training or pull-on pants are the most preferred articles herein.

Preferred articles herein have a topsheet and a backsheet, which each have a front region, back region and crotch region, positioned therein between. The absorbent structure of the invention is typically positioned in between the topsheet and backsheet. Preferred backsheets are vapour pervious but liquid impervious. Preferred topsheet materials are liquid pervious, and/or for example at least partially hydrophilic; preferred are also so-called apertured topsheets. Preferred may be that the topsheet comprises a skin care composition, e.g. a lotion. Preferred are thin absorbent articles, such as adult and infant diapers, training pants, sanitary napkins comprising an absorbent structure of the invention, the articles having an average caliper (thickness) in the crotch region of less than 1.0 cm, preferably less than 0.7 cm, more preferably less than 0.5 cm, or even less than 0.3 cm (for this purpose alone, the crotch region being defined as the central zone of the product, when laid out flat and stretched, having a dimension of 20% of the length of the article and 50% of the width of the article).

A preferred diaper herein has a front waist band and a back waist band, whereby the front waist band and back waist band each have a first end portion and a second end portion and a middle portion located between the end portions, and whereby preferably the end portions comprise each a fastening system, to fasten the front waist band to the rear waist band or whereby preferably the end portions are connected to one another, and whereby the middle portion of the back waist band and/or the back region of the backsheet and/or the crotch region of the backsheet comprises a landing member, preferably the landing member comprising second engaging elements selected from loops, hooks, slots, slits, buttons, magnets. Most preferred are hooks, adhesive or cohesive second engaging elements. Preferred may be that the engaging elements on the article, or preferably diaper are provided with a means to ensure they are only engage able at certain moments, for example, they may be covered by a removable tab, which is removed when the engaging elements are to be engaged and may be re-closed when engagement is no longer needed, as described above. Preferred diapers, including training pants, herein have one or more sets of leg elastics and/or barrier leg cuffs, as known in the art.

Superabsorbent Polymer Particles

Useful for the purposes of the present invention are in principle all particulate superabsorbent polymers known to one skilled in the art from superabsorbent literature for example as described in *Modern Superabsorbent Polymer Technology*, F. L. Buchholz, A. T. Graham, Wiley 1998. The superabsorbent particles are preferably spherical superabsorbent particles, or vienna-sausage shaped superabsorbent particles, or ellipsoid shaped superabsorbent particles of the kind typically obtained from inverse phase suspension polymerizations; they can also be optionally agglomerated at least to some extent to form larger irregular particles. Useful for the purposes of the present invention are also round-shaped particles from spray- or other gas-phase dispersion polymerizations. But most particular preference is given to commercially available irregularly shaped particles of the kind obtainable by current state of the art production processes as is more particularly described herein below by way of example.

The superabsorbent polymeric particles that are coated as described herein are preferably polymeric particles obtainable by polymerization of a monomer solution comprising i) at least one ethylenically unsaturated acid-functional monomer, ii) at least one crosslinker, iii) if appropriate one or more ethylenically and/or allylically unsaturated monomers copolymerizable with i) and iv) if appropriate one or more water-soluble polymers onto which the monomers i), ii) and if appropriate iii) can be at least partially grafted, wherein the base polymer obtained thereby is dried, classified and—if appropriate—is subsequently treated with v) at least one post-crosslinker before being dried and thermally post-crosslinked (i.e. surface cross-linked).

Useful monomers i) include for example ethylenically unsaturated carboxylic acids, such as acrylic acid, methacrylic acid, maleic acid, fumaric acid, tricarboxy ethylene and itaconic acid, or derivatives thereof, such as acrylamide, methacrylamide, acrylic esters and methacrylic esters. Acrylic acid and methacrylic acid are particularly preferred monomers. Acrylic acid is most preferable.

The superabsorbent polymers to be used according to the present invention are typically crosslinked, i.e., the polymerization is carried out in the presence of compounds having two or more polymerizable groups which can be free-radically copolymerized into the polymer network. Useful crosslinkers ii) include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in the DE-A 103 31 450, mixed acrylates which, as well as acrylate groups, comprise further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962.

Useful crosslinkers ii) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth) acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers ii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention preferably utilizes di(meth)acrylates of polyethylene glycols, the polyethylene glycol used having a molecular weight in the range from 300 g/mole to 1000 g/mole.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixedly ethoxylated or propoxylated glycerol, of altogether 3-tuply mixedly ethoxylated or propoxylated trimethylolpropane, of altogether 15-tuply ethoxylated glycerol, of altogether 15-tuply ethoxylated trimethylolpropane, of altogether at least 40-tuply ethoxylated glycerol and also of altogether at least 40-tuply ethoxylated trimethylolpropane. Where n-tuply ethoxylated means that n mols of ethylene oxide are reacted to one mole of the respective polyol with n being an integer number larger than 0.

Particularly preferred for use as crosslinkers ii) are diacrylated, dimethacrylated, triacrylated or trimethacrylated multiply ethoxylated and/or propoxylated glycerols as described for example in WO 03/104301. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels in the superabsorbent polymer (typically below 10 ppm) and the aqueous extracts of superabsorbent polymers produced therewith have an almost unchanged surface tension compared with water at the same temperature (typically not less than 0.068 N/m).

Examples of ethylenically unsaturated monomers iii) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers iv) include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide, preferably polyvinyl alcohol and starch.

Preference is given to superabsorbent polymeric particles whose base polymer is lightly crosslinked. The light degree of crosslinking is reflected in the high CRC value and also in the fraction of extractables.

The crosslinker is preferably used (depending on its molecular weight and its exact composition) in such amounts that the base polymers produced have a CRC between 20 and 60 g/g when their particle size is between 150 and 850 microns and the 16 h extractables fraction is not more than 25% by weight. The CRC is preferably between 30 and 50 g/g, more preferably between 33 and 45 g/g.

Particular preference is given to base polymers having a 16 h extractables fraction of not more than 20% by weight, preferably not more than 15% by weight, even more preferably not more than 10% by weight and most preferably not more than 7% by weight and whose CRC values are within the preferred ranges that are described above.

The preparation of a suitable base polymer and also further useful hydrophilic ethylenically unsaturated monomers i) are described in DE-A 199 41 423, EP-A 686 650, WO 01/45758 and WO 03/14300.

The reaction is preferably carried out in a kneader as described for example in WO 01/38402, or on a belt reactor as described for example in EP-A-955 086.

It is further possible to use any conventional inverse suspension polymerization process using any known suitable solvent. If appropriate, the fraction of crosslinker can be greatly reduced or completely omitted in such an inverse suspension polymerization process, since self-crosslinking occurs in such processes under certain conditions known to one skilled in the art.

It is further possible to make base polymers using any desired spray- or other gas-phase polymerization process capable of producing spherical or irregular shaped particles in a gas phase suspension of fine droplets, preferably in an inert gas phase. Inert gases are the ones described herein, organic solvent vapor and water-vapor.

The acid groups of the base polymers obtained are typically 0-100 mol %, preferably 25-100 mol %, more preferably 65-90 mol % and most preferably 68-80 mol % neutralized, for which the customary neutralizing agents can be used, for example ammonia, or amines, such as ethanolamine, diethanolamine, triethanolamine or dimethylaminoethanolamine, preferably alkali metal hydroxides, alkali metal oxides, alkali metal carbonates or alkali metal bicarbonates and also mixtures thereof, in which case sodium and potassium are particularly preferred as alkali metal salts, but most preferred is sodium hydroxide, sodium carbonate or sodium bicarbonate and also mixtures thereof. Typically, neutralization is achieved by admixing the neutralizing agent as an aqueous solution or as an aqueous dispersion or else preferably as a molten or as a solid material.

Neutralization can be carried out after polymerization, at the base polymer stage. But it is also possible to neutralize up to 40 mol %, preferably from 10 to 30 mol % and more preferably from 15 to 25 mol % of the acid groups before polymerization by adding a portion of the neutralizing agent to the monomer solution and to set the desired final degree of neutralization only after polymerization, at the base polymer stage. The monomer solution may be neutralized by admixing the neutralizing agent, either to a predetermined degree of preneutralization with subsequent post-neutralization to the final value after or during the polymerization reaction, or the monomer solution is directly adjusted to the final value by admixing the neutralizing agent before polymerization. The base polymer can be mechanically comminuted, for example by means of a meat grinder, in which case the neutralizing agent can be sprayed, sprinkled or poured on and then carefully mixed in. To this end, the gel mass obtained can be repeatedly minced for homogenization.

The neutralized base polymer is then dried with a belt, fluidized bed, tower dryer or drum dryer until the residual moisture content is preferably below 13% by weight, especially below 8% by weight and most preferably below 4% by weight, the water content being determined according to EDANA's recommended test method No. 430.2-02 "Moisture content" (EDANA=European Disposables and Nonwovens Association). The dried base polymer is thereafter ground and sieved, useful grinding apparatus typically include roll mills, pin mills, hammer mills, jet mills or swing mills.

The superabsorbent polymers to be used can be post-crosslinked in one version of the present invention. Useful post-crosslinkers v) include compounds comprising two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. Useful post-crosslinkers v) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by DE-A 103 34 584 bicyclic amide acetals, by EP-A 1 199 327 oxetanes and cyclic ureas and by WO 03/031482 morpholine-2,3-dione and its derivatives.

Post-crosslinking is typically carried out by spraying a solution of the post-crosslinker onto the base polymer or the dry base-polymeric particles. Spraying is followed by thermal drying, and the post-crosslinking reaction can take place not only before but also during or after drying.

Preferred post-crosslinkers v) are amide acetals, carbamic esters, polyhydric alcohols like diols or polyols, cyclic carbonates or bisoxazolines described for example in prior PCT application PCT/EP/05011073, which is hereby expressly incorporated herein by reference.

The at least one post-crosslinker v) is typically used in an amount of about 1.50 wt. % or less, preferably not more than 0.50% by weight, more preferably not more than 0.30% by weight and most preferably in the range from 0.001% and 0.15% by weight, all percentages being based on the base polymer, as an aqueous solution. It is possible to use a single post-crosslinker v) from the above selection or any desired mixtures of various post-crosslinkers.

The aqueous post-crosslinking solution, as well as the at least one post-crosslinker v), can typically further comprise a cosolvent. Cosolvents which are technically highly useful are $C_1$-$C_6$-alcohols, such as methanol, ethanol, n-propanol, iso-propanol, n-butanol, sec-butanol, tert-butanol or 2-methyl-1-propanol, $C_2$-$C_5$-diols, such as ethylene glycol, 1,2-propylene glycol, 1,3-propanediol or 1,4-butanediol, ketones, such as acetone, or carboxylic esters, such as ethyl acetate.

One particular embodiment does not utilize any cosolvent. The at least one post-crosslinker v) is then only employed as a solution in water, with or without an added deagglomerating aid. Deagglomerating aids are known to one skilled in the art and are described for example in DE-A-10 239 074 and also prior PCT application PCT/EP/05011073, which are each hereby expressly incorporated herein by reference. Preferred deagglomerating aids are surfactants such as ethoxylated and alkoxylated derivatives of 2-propylheptanol and also sorbitan monoesters. Particularly preferred deagglomerating aids are Plantaren® (Cognis), Span® 20, Polysorbate® 20—also referred to as Tween® 20 or polyoxyethylene 20 sorbitan monolaurate, and polyethylene glycol 400 monostearate.

The concentration of the at least one post-crosslinker v) in the aqueous post-crosslinking solution is for example in the range from 1% to 50% by weight, preferably in the range from 1.5% to 20% by weight and more preferably in the range from 2% to 5% by weight, based on the post-crosslinking solution.

In a further embodiment, the post-crosslinker is dissolved in at least one organic solvent and spray dispensed; in this case, the water content of the solution is less than 10 wt. %, preferably no water at all is utilized in the post-crosslinking solution.

It is however understood that post-crosslinkers which effect comparable surface-crosslinking results with respect to the final polymer performance may of course be used in this invention even when the water content of the solution containing such post-crosslinker and optionally a cosolvent is anywhere in the range of >0 to <100% by weight.

The total amount of post-crosslinking solution based on the base polymer is typically in the range from 0.3% to 15% by weight and preferably in the range from 2% to 6% by weight. The practice of post-crosslinking is common knowledge to those skilled in the art and described for example in DE-A-12 239 074 and also prior PCT application PCT/EP/05011073.

Spray nozzles useful for post-crosslinking are not subject to any restriction. Suitable nozzles and atomizing systems are described for example in the following literature references: Zerstäuben von Flüssigkeiten, Expert-Verlag, volume 660, Reihe Kontakt & Studium, Thomas Richter (2004) and also in Zerstäubungstechnik, Springer-Verlag, VDI-Reihe, Günter Wozniak (2002). Mono- and polydisperse spraying systems can be used. Suitable polydisperse systems include one-material pressure nozzles (forming a jet or lamellae), rotary atomizers, two-material atomizers, ultrasonic atomizers and impact nozzles. With regard to two-material atomizers, the mixing of the liquid phase with the gas phase can take place not only internally but also externally. The spray pattern produced by the nozzles is not critical and can assume any desired shape, for example a round jet, flat jet, wide angle round jet or circular ring. When two-material atomizers are used, the use of an inert gas stream will be advantageous. Such nozzles can be pressure fed with the liquid to be spray dispensed. The atomization of the liquid to be spray dispensed can in this case be effected by decompressing the liquid in the nozzle bore after the liquid has reached a certain minimum velocity. Also useful are one-material nozzles, for example slot nozzles or swirl or whirl chambers (full cone) nozzles (available for example from Düsen-Schlick GmbH, Germany or from Spraying Systems Deutschland GmbH, Germany). Such nozzles are also described in EP-A-0 534 228 and EP-A-1 191 051. One-material nozzles and two-material nozzles are sometimes also referred to as single-fluid or two-fluid nozzles, respectively.

After spraying, the superabsorbent polymeric particles are thermally dried, and the post-crosslinking reaction can take place before, during or after drying.

The spraying with the solution of post-crosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful mixers include for example Lödige® mixers, Bepex® mixers, Nauta® mixers, Processall® mixers and Schugi® mixers.

Contact dryers are preferable, shovel dryers are more preferable and disk dryers are most preferable as the apparatus in which thermal drying is carried out. Suitable dryers include for example Bepex dryers and Nara® dryers. Fluidized bed dryers can be used as well, an example being Carman® dryers.

Drying can take place in the mixer itself, for example by heating the jacket or introducing a stream of hot inert gases. It is similarly possible to use a downstream dryer, for example a tray dryer, a rotary tube oven, a continuous fluidized bed dryer, or a continuous spouted bed dryer, or a heatable screw. But it is also possible for example to utilize an azeotropic distillation as a drying process.

It is particularly preferable to apply the solution of post-crosslinker in a high speed mixer, for example of the Schugi- Flexomix® or Turbolizer® type, to the base polymer and the latter can then be thermally post-crosslinked in a reaction dryer, for example of the Nara-Paddle-Dryer type or a disk dryer (i.e. Torus-Disc Dryer®, Hosokawa). The temperature of the base polymer can be in the range from 10 to 120° C. from preceding operations, and the post-crosslinking solution can have a temperature in the range from 0 to 150° C. More particularly, the post-crosslinking solution can be heated to lower the viscosity. The preferred post-crosslinking and drying temperature range is from 30 to 220° C., especially from 120 to 210° C. and most preferably from 145 to 190° C. The preferred residence time at this temperature in the reaction mixer or dryer is preferably less than 100 minutes, more preferably less than 70 minutes and most preferably less than 40 minutes.

It is particularly preferable to utilize a continuous fluidized bed dryer or continuous spouted bed dryer for the crosslinking reaction, and the residence time is then preferably below 30 minutes, more preferably below 20 minutes and most preferably below 10 minutes.

The post-crosslinking dryer or fluidized bed dryer may be operated with air, or dehumidified air, or dried air to remove vapors efficiently from the polymer.

The post-crosslinking dryer is preferably purged with an inert gas during the drying and post-crosslinking reaction in order that vapors may be removed and oxidizing gases, such as atmospheric oxygen, may be displaced. The inert gas typically has the same limitations for relative humidity as described above for air. Mixtures of air and inert gases may also be used. To augment the drying process, the dryer and the attached assemblies are thermally well-insulated and ideally fully heated. The inside of the post-crosslinking dryer is preferably at atmospheric pressure, or else at a slight under- or overpressure.

To produce a very white polymer, the gas space in the dryer is kept as free as possible of oxidizing gases; at any rate, the volume fraction of oxygen in the gas space is not more than 14% by volume.

The superabsorbent polymeric particles can have a particle size distribution in the range from 45 µm to 4000 µm. Particle sizes used in the hygiene sector preferably range from 45 µm to 1000 µm, preferably from 45-850 µm, and especially from 100 µm to 850 µm. It is preferable to coat superabsorbent polymeric particles having a narrow particle size distribution, especially 100-850 µm, or even 100-600 µm.

Narrow particle size distributions are those in which not less than 80% by weight of the particles, preferably not less than 90% by weight of the particles and most preferably not less than 95% by weight of the particles are within the selected range; this fraction can be determined using the familiar sieve method of EDANA 420.2-02 "Particle Size Distribution". Selectively, optical methods can be used as well, provided these are calibrated against the accepted sieve method of EDANA.

Preferred narrow particle size distributions have a span of not more than 700 µm, more preferably of not more than 600 µm, and most preferably of less than 400 µm. Span here refers to the difference between the coarse sieve and the fine sieve which bound the distribution. The coarse sieve is not coarser than 850 µm and the fine sieve is not finer than 45 µm. Particle size ranges which are preferred for the purposes of the present invention are for example fractions of 150-600 µm (span: 450 µm), of 200-600 µm (span: 400 µm), of 300-600 µm (span: 300 µm), of 200-700 µm (span: 500 µm), of 150-500 µm (span: 350 µm), of 150-300 µm (span: 150 µm), of 300-700 µm (span: 400 µm), of 400-800 µm (span: 400 µm), of 100-800 µm (span: 700 µm).

Particularly preferred superabsorbent particles contain less than 3 wt. %, more preferably less than 1 wt. %, most preferably less than 0.5 wt. % particles with a particle size less than 150 µm.

Between the coarse sieve and the fines sieve, there can be additional sieves placed in the machine to increase the efficiency of screening. The superabsorbent polymeric particles may be sifted at elevated temperature by heating the screening apparatus and/or the superabsorbent particles. Preferably screening takes place under negative pressure vs. outside atmosphere to ensure fine dust containment at all times. Preferably screening takes place under dehumidified or dried air atmosphere. In another preferred embodiment screening takes place under inert gas, optionally dehumidified or dried inert gas. Screening typically takes place after grinding of the base polymer and optionally after surface-cross-linking. Screening preferably takes place before coating the superabsorbent polymeric particles with a film-forming polymer and optionally a second time after heat-treatment of the coated particles. Fine particles generated during any of the foregoing screening processes may be disposed or optionally recycled in the production process. Coarse particles may be disposed or preferably recycled in the production process. Coarse particle may be recycled by passing them through the grinding step at least one more time.

Preference is likewise given to monodisperse superabsorbent polymeric particles as obtained from the inverse suspension polymerization process. It is similarly possible to select mixtures of monodisperse particles of different diameter as superabsorbent polymeric particles, for example mixtures of monodisperse particles having a small diameter and monodisperse particles having a large diameter. It is similarly possible to use mixtures of monodisperse with polydisperse superabsorbent polymeric particles.

Coating these superabsorbent polymeric particles having narrow particle size distributions and preferably having a maximum particle size of ≤600 µm according to the present invention provides a superabsorbent material, which swells rapidly and therefore is particularly preferred.

The superabsorbent particles can be spherical in shape as well as irregularly shaped particles.

Applying the Coating Agent to a Component, E.G. Particles

The coating agent comprising the polyurethane polymer with the silica and/or modified silica as described herein may be applied as a film or coating to a component of the article herein.

It may be applied as a melt or more preferably as a solution or dispersion in an aqueous or organic liquid, for example as an aqueous dispersion, as an aqueous solution or as an organic solution to the particles of the water-absorbing addition polymer.

Useful solvents for polyurethanes include solvents, which make it possible to establish 1 to not less than 40% by weight concentrations of the polyurethane in the respective solvent or mixture. As examples there may be mentioned alcohols, esters, ethers, ketones, amides, and halogenated hydrocarbons; examples include methyl ethyl ketone, acetone, isopropanol, tetrahydrofuran, dimethylformamide, N-methylpyrrolidone, chloroform and mixtures thereof. Solvents which are polar, aprotic and boil below 100° C. are particularly advantageous.

In some embodiment, it may be preferred that the polyurethanes herein are dispersed in an aqueous liquid and then formed into a film and applied to a component or applied as a coating onto a component It is particularly preferable to coat the superabsorbent polymeric particles herein in a fluidized bed reactor. The particles are introduced as generally customary, depending on the type of the reactor, and are generally coated by spraying with coating agent, e.g. a solution or dispersion of the polyurethanes herein. Aqueous dispersions are particularly preferred for this.

The polyurethane solution or dispersion applied by spray-coating is preferably very concentrated. For this, the viscosity of this polyurethane mixture must not be too high, or the polyurethane solution or dispersion can no longer be finely dispersed for spraying. Preference is given to an aqueous polymeric dispersion especially a polyurethane solution or dispersion having a viscosity of <500 mPa·s, preferably of <300 mPa·s, more preferably of <100 mPa·s, even more preferably of <10 mPa·s, and most preferably <5 mPa·s (typically determined with a rotary viscometer at a shear rate ≥200 rpm for the polyurethane dispersion, and specifically suitable is a Haake rotary viscometer type RV20, system M5, NV). The abovementioned viscosities are preferably exhibited at a temperature of 15-40° C., more preferably at 18-25° C. However, if the dispersion or solution is sprayed at an elevated temperature it is sufficient if the abovementioned viscosities are exhibited at such elevated application temperature.

The concentration of polyurethane in the polyurethane solution or dispersion is generally in the range from 1% to 60% by weight, preferably in the range from 5% to 40% by weight and especially in the range from 10% to 30% by weight. Higher dilutions are possible, but generally lead to longer coating times. A particular advantage of polyurethane dispersions is their relatively low viscosity even at high concentrations and high molecular weights.

Fluidized bed in the context of the present invention means that the superabsorbent polymeric particles are carried upwards in erratic motion and maintained in a fluidized state by a gas stream or are maintained in an equivalent state by good mixing and reduction of density. Continuous means that uncoated particles are continuously fed to the coater and that coated particles are continuously discharged from the coater after passing all spraying-zones inside the coater. Useful fluidized bed reactors include for example the fluidized or suspended bed coaters familiar in the pharmaceutical industry. Particular preference is given to reactors using the Wurster principles or the Glatt-Zeller principles which are described for example in "Pharmazeutische Technologie, Georg Thieme Verlag, 2nd edition (1989), pages 412-413" and also in "Arzneiformenlehre, Wissenschaftliche Verlagsbuchhandlung mbH, Stuttgart 1985, pages 130-132". Particularly suitable batch and continuous fluidized bed processes on a commercial scale are described in Drying Technology, 20(2), 419-447 (2002). According to the Wurster process the particles are carried by an upwardly directed stream of carrier gas in a central tube, against the force of gravity, past at least one spray nozzle and are sprayed concurrently with the finely dispersed polyurethane solution or dispersion. The particles thereafter fall back to the base along the side walls, are collected on the base, and are again carried by the flow of carrier gas through the central tube past the spray nozzle. The spray nozzle typically sprays from the bottom into the fluidized bed, it can also project from the bottom into the fluidized bed.

According to the Glatt-Zeller process, the particles are conveyed by the carrier gas on the outside along the walls in the upward direction and then fall in the middle onto a central nozzle head, which typically comprises at least 3 two-material nozzles, which spray to the side. The particles are thus sprayed from the side, fall past the nozzle head to the base and are taken up again there by the carrier gas, so that the cycle can start anew.

The feature common to the two processes is that the particles are repeatedly carried in the form of a fluidized bed past the spray device, whereby a very thin and typically very homogeneous coating of the polyurethane can be applied. Furthermore, a carrier gas is used at all times and it has to be fed and moved at a sufficiently high rate to maintain fluidization of the particles. As a result, liquids are rapidly vaporized in the apparatus, such as for example the solvent (i.e. water) of the dispersion, even at low temperatures, whereby the polyurethane of the dispersion are laid down onto the surface of the particles.

Other embodiments, for example, may be Schuggi mixers, turbolizers or plowshare mixers, which can be used alone or preferably as a battery of plural consecutive units. In another embodiment continuous spray-mixers using the principles of theTelschig-type are used in which the spray hits free falling particles in-flight, the particles being repeatedly exposed to the spray. Suitable mixers are described in Chemie-Technik, 22 (1993), Nr. 4, p. 98 ff.

It is preferred herein that the coating takes place at a product and/or carrier gas temperature in the range from 0° C. to 150° C., preferably from 20 to 100° C., especially from 40 to 90° C. and most preferably from 50 to 80° C.

After application of the coating agent as a dispersion or solution, the liquid is removed, e.g. by drying evaporation). The polyurethane may be present in the form of particles on the surface of the component herein, and it may be preferred that said polyurethane coating is annealed, to form a film-like coating on the component. This can be done by submitting the component with polyurethane deposited thereon, e.g. s particles, o temperatures above the highest Tg of the polyurethane, and/or fro example to temperatures above 100° C.

EXAMPLES

GK 1302/61

In a reactor equipped with a mechanical stirrer, reflux condenser and a thermocouple a mixture of 400 g (0.20 mol) of a polyesterdiol made from adipic acid, neopentyl glycol and hexane diole-1,6 and having a hydroxyl number of 56, 40.2 g (0.30 mol) dimethylol propionic acid and 18.0 g (0.20 mol) butane diol-1,4 was heated at 50° C. To this mixture 200 g (0.90 mol) of isophorone diisocyanate and 80 g acetone were added and heated under stirring in an oil bath at 105° C. After 240 minutes the mixture was diluted with 800 g acetone and cooled to 30° C. 34.0 g (0.20 mol) isophorone diamine was added and stirred for 90 minutes. 20.0 g of an 25 wght % aqueous solution of ammonia was added. After 10 minutes a slurry of 100 g Aerosil 300 and 1200 g water were added. Finally the acetone was distilled off under reduced pressure.

The dispersion had a solids content of 28.6%.

GK 1302/63

In a reactor equipped with a mechanical stirrer, reflux condenser and a thermocouple a mixture of 400 g (0.20 mol) of a polyesterdiol made from adipic acid, neopentyl glycol and hexane diole-1,6 and having a hydroxyl number of 56, 40.2 g (0.30 mol) dimethylol propionic acid and 18.0 g (0.20 mol) butane diol-1,4 was heated at 50° C. To this mixture 200 g (0.90 mol) of isophorone diisocyanate and 80 g acetone were added and heated under stirring in an oil bath at 105° C. After 240 minutes the mixture was diluted with 800 g acetone and cooled to 30° C. 100 g Aerosil 300, 200 g acetone and 34.0 g (0.20 mol) isophorone diamine were added and stirred for 90 minutes. 20.0 g of an 25 wght % aqueous solution of ammonia was added. After 10 minutes 1200 g water was added. Finally the acetone was distilled off under reduced pressure.

The dispersion had a solids content of 32.9%.

GK 1302/82

In a reactor equipped with a mechanical stirrer, reflux condenser and a thermocouple a mixture of 400 g (0.20 mol) of a polyesterdiol made from adipic acid, neopentyl glycol and hexane diole-1,6 and having a hydroxyl number of 56, 20.1 g (0.15 mol) dimethylol propionic acid was heated at 50° C. To this mixture 150 g acetone and 112.6 g (0.67 mol) of hexamethylene diisocyanate-1,6 were added and heated under stirring in an oil bath at 90° C. After 180 minutes the mixture was diluted with 550 g acetone and cooled to 30° C. 12.0 g triethyl amine and 34.0 g isophorone diamine were added and stirred for 10 minutes. Then 650 g water and a slurry of 17.6 g modified Aerosil 300 in 200 g acetone was added.

For the modification, 17.6 g of Aerosil 300 was suspended in 200 g acetone. 0.88 g of 3-(aminopropyl)-trimethoxysilane was added and the slurry stirred for 120 min at 25° C.

Finally the acetone was distilled off under reduced pressure.

The dispersion had a solids content of 23.7%.

GK 1302/86

In a reactor equipped with a mechanical stirrer, reflux condenser and a thermocouple a mixture of 400 g (0.20 mol) of a polyesterdiol made from adipic acid, neopentyl glycol and hexane diole-1,6 and having a hydroxyl number of 56, 20.1 g (0.15 mol) dimethylol propionic acid was heated at 50° C. To this mixture 150 g acetone and 112.6 g (0.67 mol) of hexamethylene diisocyanate-1,6 were added and heated under stirring in an oil bath at 90° C. After 180 minutes the mixture was diluted with 550 g acetone and cooled to 30° C. 17.6 g Aerosil 300, 12.0 g triethyl amine and 34.0 g isophorone diamine was added and stirred. After 10 minutes 650 g water was added. After 10 minutes a mixture of 8.2 g diethylene triamine and 100 g water was added. Finally the acetone was distilled off under reduced pressure.

The dispersion had a solids content of 28.3%.

Films and Test Sample Preparations:

In all examples, fresh dispersions of the polyurethane with silica/modified silica (within 2 weeks of their fabrication of the polyurethane with silica or modified silica) are drawn down on a glass substrate and material quantities are selected to form films having a ~50 micron thickness on average. Films are then dried at 50 degC for 24 hrs. They are then annealed at 150 degC for 10 min. Films are removed from the glass by soaking them into a warm (60 degC) water bath; and then allowed to dry for 24 hrs. When tested in the wet state, films (or cut samples thereof) are then soaked again, in a 9% saline solution for 24 hrs.

For tensile testing and force relaxation measurements, 1×2 inch test samples are cut out of the films for testing in both the dry and wet states.

For tear propagation testing, two cutting dies are used having the following dimensions
  (as shown in FIG. 1):
  A 100 mm width×16 mm length die with a 40 mm notch, and
  A 100 mm width×16 mm length die with a 60 mm notch
Film Characterization:

Tests are performed according to the following protocol, and the data analyzed according to the following methodology.
Tensile Testing:

Tensile curves were collected using MTS Alliance RT/1 Tensile tester operated at R.T. and at a rate of 10.0 in/min (0.25 m/min)

Information extracted from the curves include the E-Modulus at 300% (represented by the amount of stress increase at 300% strain) reported in MPa, the ultimate Strain or Elongation at break (in %) and the Peak Stress or Stress at break (in MPa).
Tear Propagation Testing:

Notched film samples are cut with the appropriately dimensioned (n=3) for each die. The weight and thickness of the film pieces are measured. The notched samples are placed with the notch cut parallel to the upper grip. Test speed 0.0001 m/s, and 0.01 sec−1 initial Strain Rate By testing wide-shaped specimens having two different initial notch sizes, a and (a+Δa), up to complete fracture, it is possible to derive the difference of energy ΔE required to induce complete failure in specimens having a difference in notch size Δa, by simply integrating the energy difference between the two curves, up to their point of failure. This energy value may be considered to be equivalent to that required to propagate a tear over a distance Δa, for a film of thickness t. The total fracture area ΔA is equal to Δa/t. Under the conditions that strain at failure is found to be essentially independent of initial notch size, the Strain-energy Release Rate ($\Im$), referred to as the material's Fracture Toughness, can be rewritten as:

$$\Delta E/\Delta A = \Im$$

The fracture Toughness is reported in KJ/m$^2$
Force Relaxation Testing:

The force relaxation data are measured using an instrumented temperature-controlled load chamber, where in a strip of film is placed between grips and rapidly pulled to a fixed strain value (50% is the most typical value, although we report values at 200% strain in one of the examples) after the temperature has equilibrated to 100 degF. The drop in load is collected over a period of 10 hrs (high data sampling in the first seconds which eventually leads to a reduction in the data point acquisition over time).
MVTR Testing:

The inverted cup method is used to track the amount of 0.9% saline solution that can permeate through a film of known thickness over discrete periods of time, via a measure of the weight loss of the solution held in the cup. The data is reported either as gsm/day or normalized to g/day:

Film samples are cut to 1.5×2 inches.; 4 samples are made to obtain an average MVTR value; the thickness of the film samples are measured and recorded.

The MICA-Chamber with h 4 fans underneath (facing up), with 4 Inverted cup holders is used and conditioned as 74° C., 50% RH.

Each cup is filled with 10 ml of 0.9% saline. A film sample is placed on top of the cup and fastened with a gasket. This is repeated to obtain 4 cups with samples. Each cup and sample is weighed and then placed in the MICA chamber (inverted).

After 1 hour, each cup is weighed again—this is the zero weight, and then placed back in the chamber This step is repeated every hour, until 5 hours after the start, to have measurements weight zero and 4 additional weights per sample. The 5 hour value is averaged over the 4 samples and reported herein as MVTR value.

EXAMPLES

Example 1

Two elastomeric polyurethane dispersions and samples thereof that have comparable chemistry (similar polyether/ester polyols and diisocyanates composition) are tested:
Astacin PUMN TF GK1302-82, 3% modified silica (as above), is covalently incorporated into the polymeric chains.
Astacin PUMN TF GK1302-86, 3% dispersed silica (as above) in the pre-polymer step
This is compared to polyurethane sample Astacin PUMN TF without silica or modified silica.

|  | DRY | | | WET | | |
|---|---|---|---|---|---|---|
|  | Elong at Break (%) | E-Mod (300%) | Peak Stress (MPa) | Elong at Break (%) | E-Mod (300%) | Peak Stress (MPa) |
| Astacin PUMN TF | 470 | 4.44 | 37.5 | 560 | 0.87 | 10.8 |
| GK1302-86 | 400 | 5.58 | 35.2 | 420 | 2.30 | 17.6 |
| GK1302-82 | 470 | 3.53 | 31.4 | 490 | 1.37 | 13.6 |

Sampling of n=3 for all Film Samples

The E modulus and more over the Peak Stress (Stress at Break) for the PUMN TF is significantly lower in the wet-state than that for the sample with the modified silica of the invention, showing thus the benefit thereof.

Example 2

In this example, additional amounts of silica (2% and 4% by weight) are added to the above modified silica-containing samples of example 1 (GK1302-82). Sonication was used to disperse the additional silica in water, which was then added to achieve 5% and 7%, respectively, concentration of total modified silica and silica in the final formulations

|  | DRY | | | WET | | |
|---|---|---|---|---|---|---|
|  | Elong at Break (%) | E-Mod (300%) | Peak Stress (MPa) | Elong at Break (%) | E-Mod (300%) | Peak Stress (MPa) |
| GK1302-82 + 2% Silica (total 5% Silica) | 525 | 6.1 | 20.1 | 575 | 3.2 | 17.2 |
| GK1302-82 + 4% Silica (total 7% Silica) | 550 | 7.1 | 28.7 | 550 | 3.6 | 17.6 |

Sampling of n=3 for all Film Samples

As evidenced by the data in the table, further addition of dispersed silica to the polyurethane dispersions reinforces the films or coatings thereof, as reflected by the increase in E-Moduli.

Example 3

Two elastomeric polyurethane dispersions that have comparable chemistry (Astacin 1805-40: similar polyether/ester polyols and diisocyanates composition, but with a higher diisocyanate content than that in Example 1) but with a higher silica content compared to example 1 are prepared:
GK1302-61—Astacin 1805-40 with 12.6% modified silica is covalently incorporated into the polymeric chains
GK1302-63—Astacin 1805-40 with 12.6% Silica is dispersed into the water-based polyurethane dispersion
Two blends were created at two different ratios of the components in order to achieve the total levels of modified-silica of 5 and 7%, as follows

|  | IncorBlend-5% | IncorBlend-7% | DispBlend-5% | DispBlend-7% |
|---|---|---|---|---|
| GK1302-82 | 80% | 65% |  |  |
| GK1302-86 |  |  | 80% | 65% |
| GK1302-61 | 20% | 35% |  |  |
| GK1302-63 |  |  | 20% | 35% |

|  | DRY | | | WET | | |
|---|---|---|---|---|---|---|
|  | Elong at Break (%) | E-Mod (300%) | Peak Stress (MPa) | Elong at Break (%) | E-Mod (300%) | Peak Stress (MPa) |
| IncorBlend-5% | 468 | 12.7 | 34.9 | 506 | 5.7 | 22.1 |
| IncorBlend-7% | 395 | 20 | 32.3 | 456 | 11 | 28.1 |
| DispBlend-5% | 403 | 17.7 | 33.2 | 436 | 9.2 | 25.0 |
| DispBlend-7% | 359 | 25.5 | 34 | 366 | 15.6 | 29.0 |

The table shows the excellent mechanical performance of IncorBlend 5% and 7%, i.e. higher elongation at break, higher modulus and higher strength/peak stress.

Example 4

The tear properties for the Incorblends of Example 3 are tested using the test method described in a previous section. Furthermore, samples of the same polyurethane but with dispersed silica and without the modified-silica, where prepared from GK1302-63 (Astacin 1805-40 GK1302-63: 12.6% Silica dispersed into the water-based polyurethane dispersion) and as GK1302-86, as described above, herein referred to as DispBlend.

Two set of blends were created at two different ratios of the components in order to achieve the total levels of sub-micron of 5 and 7%; they are described below:

|  | IncorBlend-5% | IncorBlend-7% | DispBlend-5% | DispBlend-7% |
|---|---|---|---|---|
| GK1302-82 | 80% | 65% |  |  |
| GK1302-86 |  |  | 80% | 65% |
| GK1302-61 | 20% | 35% |  |  |
| GK1302-63 |  |  | 20% | 35% |

| Blend Type | Fracture Toughness $\Im$ (kJ/m2) - WET STATE |
|---|---|
| IncorBlend-5% | 49.4 |

-continued

| Blend Type | Fracture Toughness ℑ (kJ/m2) - WET STATE |
|---|---|
| IncorBlend-7% | 80.3 |
| DispBlend-5% | 29.0 |
| DispBlend-7% | 47.1 |

This shows that the polyurethanes with covalently bonded modified-silica have even more beneficial strength properties.

Example 5

In this example we report force relaxation measurements for the blends introduced in Example 4, using the test method described earlier. Force relaxation values after 10 hrs are reported for wet film samples, and for two different levels of constant applied strains: 50 and 200%.

| Blend Type | 10 hr Force Relaxation at 50% strain (%) | 10 hr Force Relaxation at 200% strain (%) |
|---|---|---|
| IncorBlend-5% | 86 | 88 |
| IncorBlend-7% | 85 | 89 |
| DispBlend-5% | 63 | 86 |
| DispBlend-7% | 66 | 86 |

In the case of coated superabsorbent polymer particles with a coating of the polyurethane materials of the invention, it is beneficial for the coatings to ultimately relax and allow minimizing the constraints applied onto the swelling coated superabsorbent polymeric particles overtime, hence maximizing the capacity of the superabsorbent to take up fluid. The above data shows that Incorblends blends are highly suitable.

Example 6

In this example, polyurethanes comprising covalently bonded modified Aerosil 300, i.e. modified with AMP's (3-aminopropyltrimethylsilane) are tested. The tensile properties are summarized below
 Astacin PUMN TF GK1566/60—9% Silica (of which 2.5% is AMP)

| | DRY | | WET | |
|---|---|---|---|---|
| FILM | Elong at Break (%) | E-Mod (300%) | Elong at Break (%) | E-Mod (300%) |
| PUMN TF (as in example 1) | 412 | 5.1 | 563 | 1.0 |
| GK1566/60 with modified Aerosil 300 | 330 | 6.7 | 450 | 2.7 |

Example 7

In this example, the use of only a cross-linking agent in the polyurethane film is compared to the use of covalently bonded modified silica. Basonat HW 180PC (BS) supplied by BASF is a modified polyisocyanate, useful as cross-linking agent. It was added directly from a 80% solution in Solvenon PC (polypropylene carbonate). The dispersion is stirred and the Basonat is added to the polyurethane dispersion.

Water Permeability data of the films as exemplified above are obtained with MICA, an instrument that enables us to perform wet MVTR. Results are reported as K' values (g/day).

| Formulations | K" (g/day) | MVTR (gsm/day) |
|---|---|---|
| PUMN TF | 0.003 | 70 |
| PUMN TF + 4% BS | 0.003 | 75 |
| IncorBlend-5% | 0.006 | 190 |
| DispBlend-7% | 0.004 | 93 |

The data shows the increase in beneficial permeability associated with the polyurethane material with covalently bonded modified silica.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising superabsorbent polymer particles, the particles comprising a film or coating containing a polyurethane polymer material, the polyurethane polymer material being produced by the process of:
 a) obtaining a dispersion or solution of a polyurethane polymer or pre-polymer in a liquid;
 b) i) adding silica-containing material modified to be capable of covalently bonding to the polyurethane polymers or pre-polymers to the dispersion or solution of step a), the material then covalently bonding to the polyurethane polymers or pre-polymers; or
  ii) adding a silica-containing material to the dispersion or solution of step a) and adding a modification material that modifies the silica-containing material to be capable of covalently bonding to the polyurethane polymers or pre-polymers to the dispersion or solution, and thereby obtaining a modified silica-containing material, the resulting material then covalently bonding to the polyurethane polymers or pre-polymers; and
 c) adding a further silica to the dispersion or solution simultaneously with step a) or step b), or subsequently to step b), the further silica not being modified to be capable of covalently bonding to the polyurethane polymers or pre-polymers;

wherein the modified silica-containing material is modified fumed silica.

2. The article according to claim 1, wherein the process further comprises the step of adding a cross-linking agent simultaneously with step a) or step b), or subsequently to step b).

3. The article according to claim 1, wherein the modified silica-containing material is present at a level from about 0.25% to about 10%, by weight, of the polyurethane polymers or pre-polymers.

4. The article according to claim 3, wherein the modified silica-containing material is present at a level from about 0.5% to about 8%, by weight, of the polyurethane polymers or pre-polymers.

5. The article according to claim 1, wherein the further silica is present at a level of about 10% or less, by weight, of the polyurethane polymers or pre-polymers.

6. The article according to claim 5, wherein the further silica is present at a level of about 5% or less, by weight, of the polyurethane polymers or pre-polymers.

7. The article according to claim 1, wherein the modified silica-containing material has a weight average particle size from about 3 nm to about 200 nm.

8. The article according to claim 7, wherein the modified silica-containing material has a weight average particle size from about 5 nm to about 100 nm.

9. The article according to claim 1, wherein the polyurethane polymers or pre-polymers of step a) comprise polyether urethanes, polyester urethanes, or both.

10. The article according to claim 1, wherein the polyurethane polymers comprise carboxylate/carboxylic acid groups capable of covalently bonding to the modified silica-containing material.

11. The article according to claim 1, wherein the polyurethane polymer material is produced by a process comprising the steps of:
   ai) obtaining a first solution or dispersion of polyurethane polymers or pre-polymers in a liquid; and
   bi) adding a further silica to the dispersion or solution of step ai) in accordance with step (c) of claim 1; and
   aii) obtaining a second solution or dispersion of polyurethane polymers or pre-polymers in a liquid; and
   bii) adding a modified silica-containing material to the dispersion or solution of step aii), in accordance with step (b) of claim 1; and
   c) combining the resulting polyurethane polymer materials of steps bi) and bii).

12. The article according to claim 1, wherein the polyurethane polymer material is produced by a process comprising the steps of:
   ai) obtaining a first solution or dispersion of polyurethane polymers or pre-polymers in a liquid; and
   bi) adding a modified silica-containing material to the dispersion or solution of step ai), in accordance with step (b) of claim 1; and
   aii) obtaining a second solution or dispersion of second polyurethane polymers or pre-polymers in a liquid; and
   bii) adding a modified silica-containing material to the dispersion or solution of step aii), in accordance with step (b) of claim 1; and
   c) combining the resulting polymeric materials of steps bi) and bii);
   wherein the polyurethane polymer or pre-polymers of step ai) are chemically different from the polyurethane polymers or pre-polymers of step aii), comprising chemically different polymerized monomers.

13. The article according to claim 1, wherein the superabsorbent polymers particles are coated with the coating containing the polyurethane polymer material by a process comprising the steps of:
   a) obtaining superabsorbent polymer particles;
   b) obtaining a dispersion of the polyurethane polymeric material in a liquid;
   c) combining the particles and the dispersion to obtain coated particles with a coating of the polyurethane polymer material;
   d) drying the coated particles of step c) to remove at least part of the liquid; and
   e) annealing the coating of the particles of step d) by heat treatment.

14. The article according to claim 13, wherein combining step c) comprises spraying the dispersion onto the particles.

15. The article according to claim 1, wherein the article comprises an infant diaper, an adult diaper, or a feminine hygiene pad.

16. The article according to claim 13, wherein the article comprises an infant diaper, an adult diaper, or a feminine hygiene pad.

17. An article comprising a film or coating containing a polyurethane polymer material, the polyurethane polymer material being produced by the process of:
   a) obtaining a dispersion or solution of a polyurethane polymer or pre-polymer in a liquid;
   b) i) adding silica-containing material modified to be capable of covalently bonding to the polyurethane polymers or pre-polymers to the dispersion or solution of step a), the material then covalently bonding to the polyurethane polymers or pre-polymers; or
   ii) adding a silica-containing material to the dispersion or solution of step a) and adding a modification material that modifies the silica-containing material to be capable of covalently bonding to the polyurethane polymers or pre-polymers to the dispersion or solution, and thereby obtaining a modified silica-containing material, the resulting material then covalently bonding to the polyurethane polymers or pre-polymers; and
   c) adding a further silica to the dispersion or solution simultaneously with step a) or step b), or subsequently to step b), the further silica not being modified to be capable of covalently bonding to the polyurethane polymers or pre-polymers;
wherein the modified silica-containing material is modified fumed silica;
wherein the article comprises a razor having a razor head comprising one or more razor blades, and the razor head comprises the film or coating containing the polyurethane polymer material.

* * * * *